United States Patent
Eggink et al.

(10) Patent No.: US 10,206,367 B2
(45) Date of Patent: Feb. 19, 2019

(54) PEPPER WITH INCREASED TOTAL CONTENT OF TERPENOIDS

(71) Applicant: RIJK ZWAAN ZAADTEELT EN ZAADHANDEL B.V., De Lier (NL)

(72) Inventors: Pieter Martijn Eggink, De Lier (NL); Jacob Pieter Willem Haanstra, De Lier (NL); Evert Willem Gutteling, De Lier (NL); Arnaud Guillaume Bovy, De Lier (NL); Yury Tikunov, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 75 days.

(21) Appl. No.: 14/979,969

(22) Filed: Dec. 28, 2015

(65) Prior Publication Data

US 2016/0130598 A1    May 12, 2016

Related U.S. Application Data

(63) Continuation-in-part of application No. PCT/EP2014/064118, filed on Jul. 2, 2014.

(30) Foreign Application Priority Data

Jul. 2, 2013   (EP) .................................... 13174801

(51) Int. Cl.
| | | |
|---|---|---|
| *A01H 5/08* | (2018.01) | |
| *C12Q 1/68* | (2018.01) | |
| *A01H 6/82* | (2018.01) | |
| *C12Q 1/6895* | (2018.01) | |
| *A01H 1/04* | (2006.01) | |
| *A01H 5/00* | (2018.01) | |
| *A23L 19/00* | (2016.01) | |

(52) U.S. Cl.
CPC ........... *A01H 6/822* (2018.05); *C12Q 1/6895* (2013.01); *A01H 1/04* (2013.01); *A01H 5/00* (2013.01); *A01H 5/08* (2013.01); *A23L 19/00* (2016.08); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 8,492,619 B2 | 7/2013 | Bar et al. |
| 9,303,271 B2 | 4/2016 | Bar et al. |
| 2010/0011458 A1 | 1/2010 | Leij |
| 2010/0227041 A1 | 9/2010 | Bar et al. |
| 2013/0298292 A1 | 11/2013 | Bar et al. |
| 2014/0173771 A1 | 6/2014 | Schuurink et al. |
| 2016/0198667 A1 | 7/2016 | Bar et al. |

FOREIGN PATENT DOCUMENTS

| | | |
|---|---|---|
| WO | 2008/152134 | 12/2008 |
| WO | 2012/169893 | 12/2012 |

OTHER PUBLICATIONS

Lefebvre et al. Genome 38: 112-121 (1995).*
Kollmannsberger et al. Journal of the Science of Food and Agriculture 91: 1598-1611 (2011).*
Paran et al. Molecular Biology 13: 251-261 (2004).*
Paavolainen et al. Plant and Soil 205: 147-154 (1998).*
Eggink et al. Theoretical and Applied Genetics 127(2): 373-390 (2014).*
Chae et al. Capsicum and Eggplant Newsletter 22: 121-124 (2003).*
Albrecht et al. HortScience 45(8): S289-S290 (Aug. 2010).*
International Search Report and Written Opinion of the International Searching Authority dated Sep. 18, 2014, which issued during prosecution of International Application No. PCT/EP2014/064118.
Database EMBL [Online] "KS09063G11 KS09 Capsicum annuum cDNA, mRNA sequence" retrieved from EBI Accession No. EM_EST:CA516765, Nov. 2002.
Database EMBL [Online]"KS12053F03 KS12 Capsicum annuum cDNA, mRNA sequence" retrieved from EBI Accession No. EM_EST:CA525343, Nov. 2002.
Database EMBL [Online] "KS09055E04 KS09 Capsicum annuum cDNA, mRNA sequence" retrieved from EBI Accession No. EM_EST:CA516285, Nov. 2002.
Database EMBL [Online] "KS26037H01 K526 Capsicum annuum cDNA, mRNA sequence" retrieved from EBI Accession No. EM_EST:GD133104, Mar. 2009.
Database EMBL [Online] "KS17036H03 KS17 Capsicum annuum cDNA, mRNA sequence" retrieved from EBI Accession No. EM_EST:GD078912, Mar. 2009.
Database EMBL [Online] "KS23026B05 KS23 Capsicum annuum cDNA, mRNA sequence" retrieved from EBI Accession No. EM_EST:GD113389, Mar. 2009.
Database EMBL [Online] "KS22027B07 KS22 Capsicum annuum cDNA, mRNA sequence" retrieved from EBI Accession No. EM_EST:GD107480, Mar. 2009.
Database EMBL [Online] "KS13034H10 KS13 Capsicum annuum cDNA, mRNA sequence" retrieved from EBI Accession No. EM_EST:GD054799, Mar. 2009.
Database EMBL [Online] "TSA: Capsicum annuum MGMT_Contig17686, mRNA sequence", retrieved from EBI Accession No. EM_TSA: JW067930, Sep. 2012.

(Continued)

*Primary Examiner* — David T Fox
(74) *Attorney, Agent, or Firm* — Duane Morris LLP; Thomas J. Kowalski; Deborah L. Lu

(57) ABSTRACT

The present invention relates to a pepper plant (*Capsicum annuum* L.) which may comprise at least one QTL selected from QTL1, QTL2 and QTL3, which when present lead to the plant producing fruits with an increased total content of terpenoids, wherein said QTL1 is obtainable from a pepper plant which may comprise said QTL representative seed of which was deposited at the NCIMB under number NCIMB 42140, and wherein said QTL2 and QTL3 are obtainable from a pepper plant which may comprise said QTL representative seed of which was deposited at the NCIMB under number NCIMB 42138.

21 Claims, 3 Drawing Sheets

Specification includes a Sequence Listing.

(56) References Cited

OTHER PUBLICATIONS

Lee, et al. "Identification of QTLs for Resistance to Anthracnose to Two Colletotrichum Species in Pepper" Journal of Crop Science and Biotechnology 13(4):227-233, Dec. 2010.
Mahasuk, et al. "Identification of Two New Genes Conferring Resistance to Colletotrichum acutatum in Capsicum baccatum" Phytopathology 99(9):1100-1104, (2009).
Moreno, et al. "HS-SPME study of the volatile fraction of Capsicum accessions and hydrids in different parts of the fruit" Scientia Horticulturae 135:87-97, Feb. 2012.
Van Den Boom, et al. "Qualitative and Quantitative Variation Among Volatile Profiles Induced by Tetranychus Feeding on Plants from Various Families" Journal of Chemical Ecology 30(1):69-89, Jan. 2004.
Wu, et al. "A Cosii Genetic map of the pepper genome provides a detailed picture of synteny with tomato and new insights into recent chromosome evolution in the genus *Capsicum*" Theoretical and Applied Genetics 118(7):1279-1293, Feb. 2009.
Yoon, et al. "Trispecies Bridge Crosses, (Capsicum annuum × C. chinense) × C. baccatum, as an Alternative for Introgression of Anthracnose Resistance from C. baccatum in C. annuum" Journal of the Korean Society for Horticultural Science 46(1):5-9, Feb. 2005.
Yoon, et al. "Overcoming Two Post-fertilization Genetic Barriers in Interspecific Hybridization between Capsicum annuum and C. baccatum for Introgression of Anthracnose Resistance" Breeding Science 56(1):31-38, Mar. 2006.

\* cited by examiner

| LG | cM | Marker | NIL36 | NIL47 | NIL35 | GNM | QTL |
|---|---|---|---|---|---|---|---|
| 1 | 0 | CA-0225 | A | A | A | A | |
| | 5.91 | CA-0082 | B | B | B | A | |
| | 6.78 | CA-1194 | B | B | B | A | |
| | 20.17 | SEQ ID NO:1 | B | B | A | A | Terpenoids |
| | 21.13 | SEQ ID NO:3 | B | B | A | A | |
| | 23.64 | SEQ ID NO:5 | B | B | A | A | |
| | 24.65 | SEQ ID NO:7 | B | B | A | A | |
| | 24.82 | SEQ ID NO:9 | B | B | A | A | |

B.

| LG | cM | Marker | NIL48 | NIL45 | NIL54 | GNM | QTL |
|---|---|---|---|---|---|---|---|
| 10.1 | 0 | SEQ ID NO:11 | A | B | B | A | |
| | 6.32 | SEQ ID NO:13 | A | B | B | A | |
| | 15.55 | SEQ ID NO:15 | B | B | B | A | Terpenoids |
| | 16.56 | SEQ ID NO:17 | B | B | B | A | |
| | 17.03 | SEQ ID NO:19 | B | B | B | A | |
| | 17.11 | SEQ ID NO:21 | B | B | B | A | |
| | 17.12 | SEQ ID NO:23 | B | B | B | A | |
| | 18.02 | SEQ ID NO:25 | B | B | B | A | |

C.

| LG | cM | Marker | NIL45 | NIL54 | GNM | QTL |
|---|---|---|---|---|---|---|
| 10.1 | 0 | SEQ ID NO:11 | B | B | A | (E)-β-Ocimene |
| | 6.32 | SEQ ID NO:13 | B | B | A | |
| | 15.55 | SEQ ID NO:15 | B | B | A | |
| | 16.56 | SEQ ID NO:17 | B | B | A | |
| | 17.03 | SEQ ID NO:19 | B | B | A | |
| | 17.11 | SEQ ID NO:21 | B | B | A | |
| | 17.12 | SEQ ID NO:23 | B | B | A | |
| | 18.02 | SEQ ID NO:25 | B | B | A | |

SEQUENCE LISTING

```
<160> NUMBER OF SEQ ID NOS: 26

<210> SEQ ID NO 1
<211> LENGTH: 82
<212> TYPE: DNA
<213> ORGANISM: Capsicum baccatum
<220> FEATURE:
<221> NAME/KEY: source
<222> LOCATION: 1..82
<223> OTHER INFORMATION: /organism="Capsicum baccatum"
      /mol_type="unassigned DNA"

<400> SEQUENCE: 1
gtgcaggcac ccctgggacc tgatatctca agtccacagc ttgttgctgc tgttgctaat      60
tctggtgctc ttggttttct ca                                              82
```

<210> SEQ ID NO 2
<211> LENGTH: 82
<212> TYPE: DNA
<213> ORGANISM: Capsicum annuum
<220> FEATURE:
<221> NAME/KEY: source
<222> LOCATION: 1..82
<223> OTHER INFORMATION: /organism="Capsicum annuum"
    /mol_type="unassigned DNA"

<400> SEQUENCE: 2
gtgcaggcac ccctgggacc tgatatctca agtccacatc ttgttgctgc tgttgctaat    60
tctggtgctc ttggttttct ca                                            82

<210> SEQ ID NO 3
<211> LENGTH: 94
<212> TYPE: DNA
<213> ORGANISM: Capsicum baccatum
<220> FEATURE:
<221> NAME/KEY: source
<222> LOCATION: 1..94
<223> OTHER INFORMATION: /organism="Capsicum baccatum"
    /mol_type="unassigned DNA"

<400> SEQUENCE: 3
gttgattatc cttgcaagca ctgaaactga tggccctgcc accacttgtg cccttataag    60
tgccggatag ggatctgtta tcatcccatt tgtt                                94

<210> SEQ ID NO 4
<211> LENGTH: 94
<212> TYPE: DNA
<213> ORGANISM: Capsicum annuum
<220> FEATURE:
<221> NAME/KEY: source
<222> LOCATION: 1..94
<223> OTHER INFORMATION: /organism="Capsicum annuum"
    /mol_type="unassigned DNA"

<400> SEQUENCE: 4
gttgattatc cttgcaagca ctgaaactga tggccctgac accacttgtg cccttataag    60
tgccggatag ggatctgtta tcatcccatt tgtt                                94

<210> SEQ ID NO 5
<211> LENGTH: 98
<212> TYPE: DNA
<213> ORGANISM: Capsicum baccatum
<220> FEATURE:
<221> NAME/KEY: source
<222> LOCATION: 1..98
<223> OTHER INFORMATION: /organism="Capsicum baccatum"
    /mol_type="unassigned DNA"

<400> SEQUENCE: 5
tgatgctcat acacactctc cacgagttga ggaatcaact tactcaggaa gtgcaaagcg    60
atttgtaagc gtcttgtcta agccggtgaa caacaaac                            98

<210> SEQ ID NO 6
<211> LENGTH: 98
<212> TYPE: DNA
<213> ORGANISM: Capsicum annuum
<220> FEATURE:
<221> NAME/KEY: source
<222> LOCATION: 1..98
<223> OTHER INFORMATION: /organism="Capsicum annuum"
    /mol_type="unassigned DNA"

<400> SEQUENCE: 6
tgatgctcat acacactctc cacgagttga ggaatcaact tactcaggaa gttcaaagcg    60
atttgtaagc gtcttgtcta agccggtgaa caacaaac                            98

<210> SEQ ID NO 7
<211> LENGTH: 80
<212> TYPE: DNA
<213> ORGANISM: Capsicum baccatum
<220> FEATURE:
<221> NAME/KEY: source
<222> LOCATION: 1..80
<223> OTHER INFORMATION: /organism="Capsicum baccatum"
      /mol_type="unassigned DNA"

<400> SEQUENCE: 7
cgcatacctt gccccttctt tggggtctgs tgttgttcca acagaaacaa cctccagatc    60
ctgattcata tcccctgcag                                                80

<210> SEQ ID NO 8
<211> LENGTH: 80
<212> TYPE: DNA
<213> ORGANISM: Capsicum annuum
<220> FEATURE:
<221> NAME/KEY: source
<222> LOCATION: 1..80
<223> OTHER INFORMATION: /organism="Capsicum annuum"
      /mol_type="unassigned DNA"

<400> SEQUENCE: 8
cgcatacctt gccccttctt tggggtctgs tgttgttcca acagaaacaa cctccggatc    60
ctgattcata tcccctgcag                                                80

<210> SEQ ID NO 9
<211> LENGTH: 98
<212> TYPE: DNA
<213> ORGANISM: Capsicum baccatum
<220> FEATURE:
<221> NAME/KEY: source
<222> LOCATION: 1..98
<223> OTHER INFORMATION: /organism="Capsicum baccatum"
      /mol_type="unassigned DNA"

<400> SEQUENCE: 9
tttgtaagga tttcccaaga tcattcatca aagctattct ccccaaacaa acgacttcgt    60
tccaacttgg gttccaccaa tttcagttgg ggttgttt                            98

<210> SEQ ID NO 10
<211> LENGTH: 98
<212> TYPE: DNA
<213> ORGANISM: Capsicum annuum
<220> FEATURE:
<221> NAME/KEY: source
<222> LOCATION: 1..98
<223> OTHER INFORMATION: /organism="Capsicum annuum"
      /mol_type="unassigned DNA"

<400> SEQUENCE: 10
tttgtaagga tttcccaaga tcattcatca aagctattct ccccaaacaa acaacttcgt    60
tccaacttgg gttccaccaa tttcagttgg ggttgttt                            98

<210> SEQ ID NO 11
<211> LENGTH: 100
<212> TYPE: DNA
<213> ORGANISM: Capsicum baccatum

```
<220> FEATURE:
<221> NAME/KEY: source
<222> LOCATION: 1..100
<223> OTHER INFORMATION: /organism="Capsicum baccatum"
      /mol_type="unassigned DNA"

<400> SEQUENCE: 11
gctcctagtt ccacaggagc cgatggagag gcacataact actttggtga agcagaattt    60
gcaagatgta acggctgctg aatttaaaat gttcatggac                         100

<210> SEQ ID NO 12
<211> LENGTH: 100
<212> TYPE: DNA
<213> ORGANISM: Capsicum annuum
<220> FEATURE:
<221> NAME/KEY: source
<222> LOCATION: 1..100
<223> OTHER INFORMATION: /organism="Capsicum annuum"
      /mol_type="unassigned DNA"

<400> SEQUENCE: 12
gctcctagtt ccacaggagc cgatggagag gcacataact actttggtga agaagaattt    60
gcaagatgta acggctgctg aatttaaaat gttcatggac                         100

<210> SEQ ID NO 13
<211> LENGTH: 119
<212> TYPE: DNA
<213> ORGANISM: Capsicum baccatum
<220> FEATURE:
<221> NAME/KEY: source
<222> LOCATION: 1..119
<223> OTHER INFORMATION: /organism="Capsicum baccatum"
      /mol_type="unassigned DNA"

<400> SEQUENCE: 13
gatgcaaaca acmarraaar ramaaaawtc cgttcacgag caaagaacct cgtgaagcaa    60
ctctaaataa gctttacctg ataggttggg agcccaacat ctcaccacaa agatccaac   119

<210> SEQ ID NO 14
<211> LENGTH: 119
<212> TYPE: DNA
<213> ORGANISM: Capsicum annuum
<220> FEATURE:
<221> NAME/KEY: source
<222> LOCATION: 1..119
<223> OTHER INFORMATION: /organism="Capsicum annuum"
      /mol_type="unassigned DNA"

<400> SEQUENCE: 14
gatgcaaaca acmarraaar ramaaaawtc cgttcacgag caaagaactt cgtgaagcaa    60
ctctaaataa gctttacctg ataggttggg agcccaacat ctcaccacaa agatccaac   119

<210> SEQ ID NO 15
<211> LENGTH: 107
<212> TYPE: DNA
<213> ORGANISM: Capsicum baccatum
<220> FEATURE:
<221> NAME/KEY: source
<222> LOCATION: 1..107
<223> OTHER INFORMATION: /organism="Capsicum baccatum"
      /mol_type="unassigned DNA"

<400> SEQUENCE: 15
gagcatctta tttgaagacc aagaagggga aaaagggttt caaaggtggc aaaaagggca    60
ggggaaatgg aaatggaaag ggaaggaaag gctgattgca gcttatc                107
```

```
<210> SEQ ID NO 16
<211> LENGTH: 107
<212> TYPE: DNA
<213> ORGANISM: Capsicum annuum
<220> FEATURE:
<221> NAME/KEY: source
<222> LOCATION: 1..107
<223> OTHER INFORMATION: /organism="Capsicum annuum"
      /mol_type="unassigned DNA"

<400> SEQUENCE: 16
gagcatctta tttgaagacc aagaagggga aaaagggttt caaaggtggc aaaaaaggca      60
ggggaaatgg aaatggaaag ggaaggaaag gctgattgca gcttatc                  107

<210> SEQ ID NO 17
<211> LENGTH: 118
<212> TYPE: DNA
<213> ORGANISM: Capsicum baccatum
<220> FEATURE:
<221> NAME/KEY: source
<222> LOCATION: 1..118
<223> OTHER INFORMATION: /organism="Capsicum baccatum"
      /mol_type="unassigned DNA"

<400> SEQUENCE: 17
gaaagggaca atgatgacaa cggtagtgct tttttacyra stgatgatga gacttatgca      60
aagccttgac cagggagtcc tttagttcca ccttacttgt ttwttgtttt atttgtgg      118

<210> SEQ ID NO 18
<211> LENGTH: 118
<212> TYPE: DNA
<213> ORGANISM: Capsicum annuum
<220> FEATURE:
<221> NAME/KEY: source
<222> LOCATION: 1..118
<223> OTHER INFORMATION: /organism="Capsicum annuum"
      /mol_type="unassigned DNA"

<400> SEQUENCE: 18
gaaagggaca atgatgacaa cggtagtgct tttttacyra stgatgatga gacttataca      60
aagccttgac cagggagtcc tttagttcca ccttacttgt ttwttgtttt atttgtgg      118

<210> SEQ ID NO 19
<211> LENGTH: 107
<212> TYPE: DNA
<213> ORGANISM: Capsicum baccatum
<220> FEATURE:
<221> NAME/KEY: source
<222> LOCATION: 1..107
<223> OTHER INFORMATION: /organism="Capsicum baccatum"
      /mol_type="unassigned DNA"

<400> SEQUENCE: 19
ccatctgaaa tcctccaaca agaatacaac atgacactca aggctcaagc tatactagca      60
aaagttgtgg tcattataac gtgcattaca agatggccaa aaagctc                  107

<210> SEQ ID NO 20
<211> LENGTH: 107
<212> TYPE: DNA
<213> ORGANISM: Capsicum annuum
<220> FEATURE:
<221> NAME/KEY: source
<222> LOCATION: 1..107
<223> OTHER INFORMATION: /organism="Capsicum annuum"
      /mol_type="unassigned DNA"
```

<400> SEQUENCE: 20
ccatctgaaa tcctccaaca agaatacaac atgacactca aggctcaagc tgtactagca    60
aaagttgtgg tcattataac gtgcattaca agatggccaa aaagctc    107

<210> SEQ ID NO 21
<211> LENGTH: 106
<212> TYPE: DNA
<213> ORGANISM: Capsicum baccatum
<220> FEATURE:
<221> NAME/KEY: source
<222> LOCATION: 1..106
<223> OTHER INFORMATION: /organism="Capsicum baccatum"
      /mol_type="unassigned DNA"

<400> SEQUENCE: 21
tccccaagct tataaacact tcgtcaagag ctgccacctc atcgatggtg acggtaacgt    60
tggcactctt cgtgaagtcc gagtcatctc cgggctgcca gctgtt    106

<210> SEQ ID NO 22
<211> LENGTH: 106
<212> TYPE: DNA
<213> ORGANISM: Capsicum annuum
<220> FEATURE:
<221> NAME/KEY: source
<222> LOCATION: 1..106
<223> OTHER INFORMATION: /organism="Capsicum annuum"
      /mol_type="unassigned DNA"

<400> SEQUENCE: 22
tccccaagct tataaacact tcgtcaagag ctgccacctc atcgatggtg atggtaacgt    60
tggcactctt cgtgaagtcc gagtcatctc cgggctgcca gctgtt    106

<210> SEQ ID NO 23
<211> LENGTH: 105
<212> TYPE: DNA
<213> ORGANISM: Capsicum baccatum
<220> FEATURE:
<221> NAME/KEY: source
<222> LOCATION: 1..105
<223> OTHER INFORMATION: /organism="Capsicum baccatum"
      /mol_type="unassigned DNA"

<400> SEQUENCE: 23
tgtactaact catgccctct tcttaccatc ggagtttgtt ctctccgttc cgcaattgcc    60
agagcggacg aaaaaccgcc tgagagtacg ccgcaacctc tgtcg    105

<210> SEQ ID NO 24
<211> LENGTH: 105
<212> TYPE: DNA
<213> ORGANISM: Capsicum annuum
<220> FEATURE:
<221> NAME/KEY: source
<222> LOCATION: 1..105
<223> OTHER INFORMATION: /organism="Capsicum annuum"
      /mol_type="unassigned DNA"

<400> SEQUENCE: 24
tgtactaact catgccctct tcttaccatc ggagtttgtt ctctccgttc agcaattgcc    60
agagcggacg aaaaaccgcc tgagagtacg ccgcaacctc tgtcg    105

<210> SEQ ID NO 25
<211> LENGTH: 140
<212> TYPE: DNA

```
<213> ORGANISM: Capsicum baccatum
<220> FEATURE:
<221> NAME/KEY: source
<222> LOCATION: 1..140
<223> OTHER INFORMATION: /organism="Capsicum baccatum"
      /mol_type="unassigned DNA"

<400> SEQUENCE: 25
cgtcatcatc gtcatcttca tcagcatctt caccaccaaa cctytggttc atcaaatctt    60
ccctggaata catttgcata ccgggggctc caggcatatc ctgaaggcaa aatgttgtaa   120
atttcaaatt ctgactcacg                                               140

<210> SEQ ID NO 26
<211> LENGTH: 140
<212> TYPE: DNA
<213> ORGANISM: Capsicum annuum
<220> FEATURE:
<221> NAME/KEY: source
<222> LOCATION: 1..140
<223> OTHER INFORMATION: /organism="Capsicum annuum"
      /mol_type="unassigned DNA"

<400> SEQUENCE: 26
cgtcatcatc gtcatcttca tcagcatctt caccaccaaa cctytggttc atcaaatctt    60
ccctggaata catttgcata ccaggggctc caggcatatc ctgaaggcaa aatgttgtaa   120
atttcaaatt ctgactcacg                                               140
```

PEPPER WITH INCREASED TOTAL CONTENT OF TERPENOIDS

RELATED APPLICATIONS AND INCORPORATION BY REFERENCE

This application is a continuation-in-part application of international patent application Serial No. PCT/EP2014/064118 filed 2 Jul. 2014, which published as PCT Publication No. WO 2015/000992 on 8 Jan. 2015, which claims benefit of European patent application Serial No. 13174801.4 filed 2 Jul. 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Nov. 23, 2015, is named 43104002230_SL.txt and is 8,933 bytes in size.

FIELD OF THE INVENTION

The invention relates to plants producing fruits with an increased total content of terpenoids. Furthermore the invention relates to the use of plants, seeds and propagation material from the pepper plant that may comprise the said genetic determinant as germplasm in a breeding program aimed at acquiring pepper plants producing fruits with increased terpenoid content.

BACKGROUND OF THE INVENTION

Sweet and hot pepper plants belong to the genus *Capsicum* which is part of the Nightshade family (Solanaceae). *Capsicum* species are native to South America, Middle America and a part of North America, where they have been cultivated for thousands of years, and are now cultivated worldwide. Several of the members of the *Capsicum* genus are used as spices, vegetables, and/or medicines.

The species *Capsicum annuum* L. is the most common and extensively cultivated of the five domesticated *Capsicum* species (*Capsicum annuum, Capsicum baccatum, Capsicum pubescens, Capsicum chinense, Capsicum frutescens*). It may comprise several cultivar groups among which bell pepper (also named paprika) is the most commonly grown in northern Europe and the USA. Bell pepper fruits are eaten raw, cooked, immature and mature and may be processed into powders, sauces, and salsas. The fruits are mostly green in the immature stage, but during ripening they become red, yellow, orange, purple or brown. Sweet pepper may comprise any pepper plant, such as bell pepper plants, having mild non-pungent fruits. Pepper plants can be cultivated in the open field, greenhouse, tunnel or shade house under a wide range of climatic conditions, but they perform best in warm and dry conditions.

Pepper fruits are commonly used in the diet because of their typical colors, pungency, taste and/or distinct aroma. Pepper fruits are eaten fresh or processed, as unripe (green or white) or ripe (e.g. red, yellow and orange) fruits. In the breeding of pepper, the factors production and quality (e.g. disease resistance, shelf life and firmness) are of main interest.

Pepper (*Capsicum annuum* L.) cultivation is troubled by several pests and by diseases caused by fungi, bacteria and viruses. A major problem resulting in great economic losses are infection with fungi like *Colletotrichum* causing anthracnose and *Fusarium* causing internal fruit rot. Several insects and mites are problems in cultivation, amongst them *thrips*, spider mites, aphids, white flies and leaf miners, which can result in severe yield losses.

Citation or identification of any document in this application is not an admission that such document is available as prior art to the present invention.

SUMMARY OF THE INVENTION

In the research leading to the invention new pepper plants were developed that were found to produce fruits with an increased total content of terpenoids, in particular an increased total content of monoterpenoids.

For some of these elevated monoterpenes (Table 1) specific relations with relevant pepper pathogens have already been described. E.g. in cucumber (*Cucumis sativus*) a positive correlation was found between the attraction of predatory mites (*Phytoseiulus persimilis*) and the amount of emitted (E)-β-ocimene, after infestation of the plants with herbivorous spider mites (*Tetranychus urticae*; Kappers et al., J. Chem. Ecol. (2011) 37, 150-160). In addition, antimicrobial properties related to monoterpenes have been reported in several studies of essential oils. Perez-Sanchez et al. (Food Sci. Tech. Int. (2007) 13, 341-347) e.g. reported a clear growth inhibition of the pathogenic fungi *Colletotrichum acutatum* and *Fusarium oxysporum* (causing anthracnose and internal fruit rot, respectively, in pepper), which showed the highest correlation with the concentration of the monoterpene α-terpinene, extracted from the oil of *Thymus zygis*. These examples indicate that the plants of the invention having an increased total content of terpenoids have an advantage in relation to pathogen infestation in comparison to plants that do not have such increased terpenoid content.

It was found that the increased total content of terpenoids correlated with the presence in the *Capsicum annuum* genome of an introgression from *Capsicum baccatum*, either on Linkage Group 1 (LG1) or on Linkage Group 10.1 (LG10.1), identified herein as Quantitative Trait Locus 1 (QTL1 on LG1), QTL2 and QTL3 (both on LG10.1), respectively. Nomenclature of linkage groups is referred to the consensus chromosome numbers as in Wu et al. (Theor. Appl. Genet. (2009) 118, 1279-1293). Linkage Group 10.1 represents a part of chromosome 10. QTL1 that causes the increased total content of terpenoids is as present in the genome of plants grown from seeds of which a representative sample was deposited at the NCIMB under accession number NCIMB 42140. This QTL is located on LG1 and in the genome of plants grown from seeds of deposit NCIMB 42140 is linked to at least one marker selected from the group consisting of SEQ ID No:1, SEQ ID No:3, SEQ ID No:5, SEQ ID No:7 and SEQ ID No:9 (Table 1).

QTL2 that also causes the increased total content of terpenoids is as present in the genome of plants grown from seeds of which a representative sample was deposited at the NCIMB under accession number NCIMB 42138. This QTL is located on LG10.1 (LG10.1) and in the genome of plants grown from seeds of deposit NCIMB 42138 is linked to at least one marker selected from the group consisting of SEQ ID No:15, SEQ ID No:17, SEQ ID No:19, SEQ ID No:21, SEQ ID No:23 and SEQ ID No:25 (Table 1).

The telomeric region of LG10.1 was found to harbor a further QTL (QTL3) that causes the increased content of the monoterpenoid (E)-β-ocimene. QTL3 is as present in the genome of plants grown from seeds of which a representative sample was deposited at the NCIMB under accession number NCIMB 42138. In the genome of plants grown from seeds of deposit NCIMB 42138 QTL3 is linked to a marker of SEQ ID No:11 and/or SEQ ID No:13 (Table 1).

The invention thus relates to a pepper plant (*Capsicum annuum* L.) that produces fruits with an increased total content of terpenoids as a result of the presence in the genome of the pepper plant of at least one QTL selected from QTL1, QTL2 and QTL3, wherein:
  QTL1 is the same or similar to the QTL that in the genome of plants grown from seeds of deposit NCIMB 42140 is located on LG1 and is linked therein to at least one marker selected from the group consisting of SEQ. No:1, SEQ ID No:3, SEQ ID No:5, SEQ ID No:7 and SEQ ID No:9;
  QTL2 is the same or similar to the QTL that in the genome of plants grown from seeds of deposit NCIMB 42138 is located on LG10.1 and is linked therein to at least one marker selected from the group of SEQ ID No:15, SEQ ID No:17, SEQ ID No:19, SEQ ID No:21, SEQ ID No:23 and SEQ ID No:25; and
  QTL3 is the same or similar to the QTL that in the genome of plants grown from seeds of deposit NCIMB 42138 is located on LG10.1 and is linked therein to at least one marker selected from the group of SEQ ID No:11 and SEQ ID No:13.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Seeds of *Capsicum annuum* L. line 11R.6968-00 that comprise QTL1 and line 11R.6921-00 that comprise QTL2 and QTL3 which QTL each leads to the pepper plant producing fruits that have an increased total content of terpenoids, were deposited with NCIMB Ltd, Ferguson Building, Craibstone Estate, Bucksburn, Aberdeen AB21 9YA, UK, on Apr. 12, 2013 under deposit accession numbers NCIMB 42140 and NCIMB 42138, respectively. Seeds of deposit NCIMB 42140 comprise QTL1 on LG1 in a homozygous state, while seeds of deposit NCIMB 42138 comprise QTL2 and QTL3 on LG10.1 in a homozygous state.

The deposited seeds do not meet the DUS criteria which are required for obtaining plant variety protection, and can therefore not be considered to be plant varieties.

The Deposits with NCIMB Ltd, under deposit accession number deposit accession numbers NCIMB 42140 and NCIMB 42138 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: Graphical representation of the selected QTLs of the invention: A. QTL1 on LG1, B. QTL2 on LG10.1 and C. QTL3 on LG10.1.

*C. baccatum* introgressions are indicated with their markers as B (homozygous, in bold), while the *C. annuum* genomic background is indicated with A.

Figure 2:
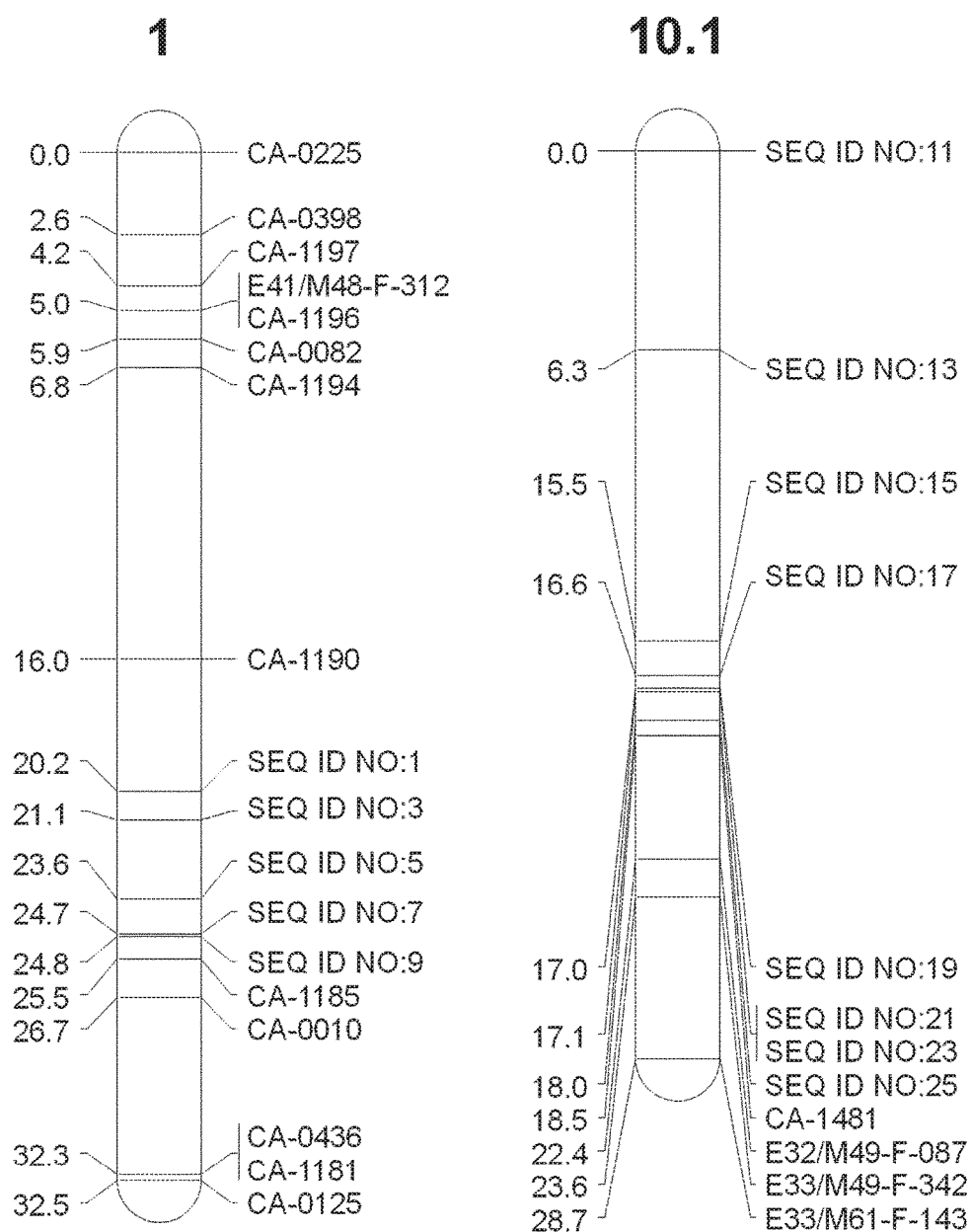

FIG. 2: Genetic maps of the *C. annuum*×*C. baccatum* BC$_2$ population Linkage Group 1 (LG1) and Linkage Group 10.1 (LG10.1).

Figure 3:
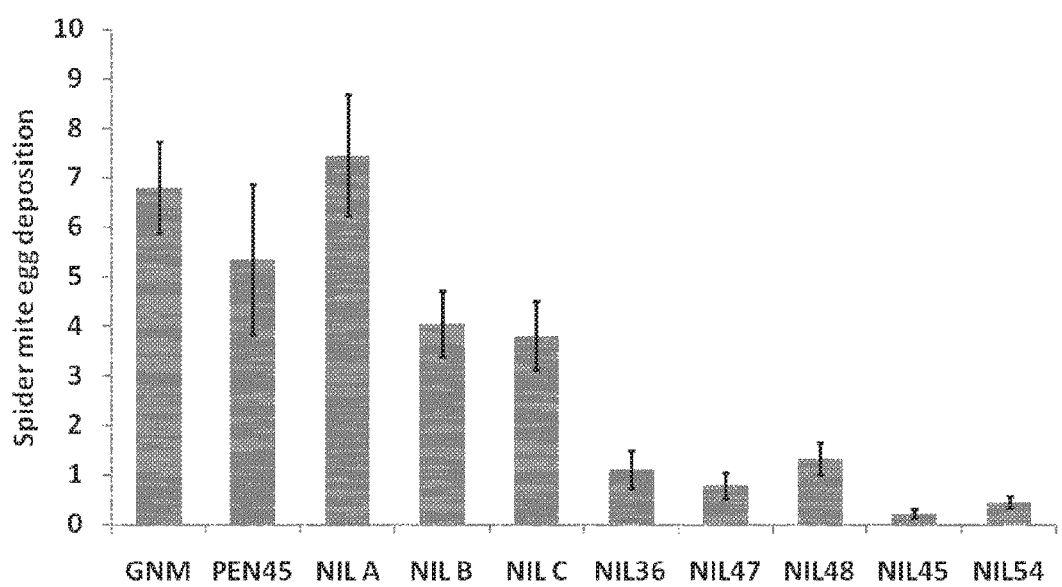

FIG. 3: Number of eggs (±standard error) laid by a single synchronized female spider mite during 5 days on leaf discs of different *Capsicum* accessions. N=9 for each of three experimental replicates. *Capsicum* accessions that were tested were: recurrent *Capsicum annuum* parent GNM, *Capsicum baccatum* var. *pendulum* accession PEN45; three randomly selected NILS not carrying any QTL of the invention (NIL A, NIL B and NIL C); NIL36 and NIL47 with introgression LG1 (QTL1) and NIL48 (QTL2) and NIL45 and NIL54 (QTL2 plus QTL3) with introgression LG10.1.

DETAILED DESCRIPTION OF THE INVENTION

The invention thus relates to a pepper plant (*Capsicum annuum* L.) that produces fruits with an increased total content of terpenoids as a result of the presence in the genome of the pepper plant of at least one QTL selected from QTL1, QTL2 and QTL3, wherein:

QTL1 is the same or similar to the QTL that in the genome of plants grown from seeds of deposit NCIMB 42140 is located on LG1 and is linked therein to at least one marker selected from the group consisting of SEQ. No:1, SEQ ID No:3, SEQ ID No:5, SEQ ID No:7 and SEQ ID No:9;

QTL2 is the same or similar to the QTL that in the genome of plants grown from seeds of deposit NCIMB 42138 is located on LG10.1 and is linked therein to at least one marker selected from the group of SEQ ID No:15, SEQ ID No:17, SEQ ID No:19, SEQ ID No:21, SEQ ID No:23 and SEQ ID No:25; and QTL3 is the same or similar to the QTL that in the genome of plants grown from seeds of deposit NCIMB 42138 is located on LG10.1 and is linked therein to at least one marker selected from the group of SEQ ID No:11 and SEQ ID No:13.

Preferably, the pepper plant of the invention is a sweet pepper.

In this context "the same" means that the QTL has the same sequence as in the deposit. "Similar" means that the sequence in the plant of the invention may have minor alterations that do not affect the function of the QTL. In a preferred embodiment the QTLs in the plants of the invention are the same as the QTLs in the deposited material.

The development of the initial plants with the increased total content of terpenoids is described in Example 1. In short, Capsicum baccatum var. pendulum was used as a donor parent for backcrossing (BC) with two cultivated C. annuum blocky breeding lines (SM and GNM). Further to this initial cross $BC_2S_1$ lines and near-isogenic lines (NILS) were developed that were further tested for terpenoid content and in some of these lines plants producing fruits with an increased total terpenoids content were identified. Surprisingly, these plants produced fruits with a total terpenoid content, in particular total monoterpenoid content, that was significantly higher than that of any of the parents (Capsicum baccatum var. pendulum, SM and GNM) of the crosses that generated them.

Plants of the invention were found to comprise at least one of three introgressions from Capsicum baccatum on LG1 and LG10.1, the QTLs of the invention. All introgressions have major effects on terpenoid content of mature pepper fruits, in particular on monoterpenoid content, together affecting the concentration of at least fifteen different monoterpenes. The size of the LG1 and LG10.1 introgression fragment is 4.6 cM for QTL1, whereas the size of the LG10.1 introgression fragments is 2.5 cM for QTL2 and 6.3 cM for QTL3. QTL2 and QTL3 together are located on an introgression fragment of 18.0 cM. These sizes are based on the genetic map (FIG. 2) developed within the research leading to this invention. The availability of in-fragment markers facilitates their use in breeding.

It was found that in the genome of plants grown from seeds of deposit NCIMB 42140 each of the markers SEQ ID No:1, SEQ ID No:3, SEQ ID No:5, SEQ ID No:7 and SEQ ID No:9 (full sequence data given in Table 1) is linked to the first QTL, QTL1, that causes the fruits to have the increased total terpenoid content of the invention (FIG. 1A). Although any of these markers or any combination of these markers may be used for identifying QTL1 causing the invented trait of an increased total terpenoid content, marker SEQ ID NO:1 is preferred because it had the highest LOD score in the statistical tests. QTL1 causing the invented trait of an increased total terpenoid content may be identified using the combination of markers SEQ ID No:1, SEQ ID No:3, SEQ ID No:5, SEQ ID No:7 and SEQ ID No:9, the combination of markers SEQ ID No:1, SEQ ID No:3, SEQ ID No:5 and SEQ ID No:7, the combination of markers SEQ ID No:1, SEQ ID No:3, SEQ ID No:5 and SEQ ID No:9, the combination of markers SEQ ID No:1, SEQ ID No:3, SEQ ID No:7 and SEQ ID No:9, the combination of markers SEQ ID No:1, SEQ ID No:5, SEQ ID No:7 and SEQ ID No:9, the combination of markers SEQ ID No:1, SEQ ID No:3 and SEQ ID No:5, the combination of markers SEQ ID No:1, SEQ ID No:3 and SEQ ID No:7, the combination of markers SEQ ID No:1, SEQ ID No:3 and SEQ ID No:9, the combination of markers SEQ ID No:1, SEQ ID No:5 and SEQ ID No:7, the combination of markers SEQ ID No:1, SEQ ID No:5 and SEQ ID No:9, the combination of markers SEQ ID No:1, SEQ ID No:7 and SEQ ID No:9, the combination of markers SEQ ID No:1 and SEQ ID No:3, the combination of markers SEQ ID No:1 and SEQ ID No:5, the combination of markers SEQ ID No:1 and SEQ ID No:7, the combination of markers SEQ ID No:1 and SEQ ID No:9. In particular, QTL1 causing the invented trait of novel flavour can be identified using the combination of markers SEQ ID No:1, SEQ ID No:3, SEQ ID No:5, SEQ ID No:7 and SEQ ID No:9, more in particular SEQ ID No:1, SEQ ID No:3 and SEQ ID No:5, and most in particular SEQ ID No:1 and SEQ ID No:3.

Moreover, it was found that in the genome of plants grown from seeds of deposit NCIMB 42138 each of the markers, SEQ ID No:15, SEQ ID No:17, SEQ ID No:19, SEQ ID No:21, SEQ ID No:23 and SEQ ID No:25 (full sequence data given in Table 1) is linked to the second QTL, QTL2, that also causes the fruits to have the increased total terpenoid content of the invention (FIG. 1B). Although any of these markers or any combination of these markers may be used for identifying QTL2 causing the invented trait of an increased total terpenoid content, marker SEQ ID NO:17 is preferred because it had the highest LOD score in the statistical tests. QTL2 causing the invented trait of an increased total terpenoid content may be identified using the combination of markers SEQ ID No:15, SEQ ID No:17, SEQ ID No:19, SEQ ID No:21, SEQ ID No:23 and SEQ ID No:25, the combination of markers SEQ ID No:17, SEQ ID No:15, SEQ ID No:19, SEQ ID No: 21 and SEQ ID No:23, the combination of markers SEQ ID No:17, SEQ ID No:15, SEQ ID No:19, SEQ ID No: 21 and SEQ ID No:25, the combination of markers SEQ ID No:17, SEQ ID No:15, SEQ ID No:19, SEQ ID No: 21 and SEQ ID No:23, the combination of markers SEQ ID No:17, SEQ ID No:15, SEQ ID No:19 and SEQ ID No: 21, the combination of markers SEQ ID No:17, SEQ ID No:15, SEQ ID No:19 and SEQ ID No: 25, the combination of markers SEQ ID No:17, SEQ ID No:15, SEQ ID No:21 and SEQ ID No: 25, the combination of markers SEQ ID No:17, SEQ ID No:19, SEQ ID No:21 and SEQ ID No: 25, the combination of markers SEQ ID No:17, SEQ ID No:15, SEQ ID No:19 and SEQ ID No: 23, the combination of markers SEQ ID No:17, SEQ ID No:15, SEQ ID No:21 and SEQ ID No: 23, the combination of markers SEQ ID No:17, SEQ ID No:19, SEQ ID No:21 and SEQ ID No: 23, the combination of markers SEQ ID No:17, SEQ ID No:15, SEQ ID No:23 and SEQ ID No: 25, the combination of markers SEQ ID No:17, SEQ ID No:19, SEQ ID No:23 and SEQ ID No: 25, the combination of markers SEQ ID No:17, SEQ ID No:21, SEQ ID No:23 and SEQ ID No: 25, the combination of markers SEQ ID No:17, SEQ ID No:15 and SEQ ID No:19, the combination of markers SEQ ID No:17, SEQ ID No:15 and SEQ ID No:21, the combination of markers SEQ ID No:17, SEQ ID No:15 and SEQ ID No:23, the combination of markers SEQ ID No:17, SEQ ID No:15 and SEQ ID No:25, the combination of markers SEQ ID No:17, SEQ ID No:19 and SEQ ID No:21, the combination of markers SEQ ID No:17, SEQ ID No:19 and SEQ ID No:23, the combination of markers SEQ ID No:17, SEQ ID No:19 and SEQ ID No:25, the combination of markers SEQ ID No:17, SEQ ID No:21 and SEQ ID No:23, the combination of markers SEQ ID No:17, SEQ ID No:21 and SEQ ID No:25, the combination of markers SEQ ID No:17, SEQ ID No:23 and SEQ ID No:25, the combination of markers SEQ ID No:17 and SEQ ID No:15, the combination of markers SEQ ID No:17 and SEQ ID No:19, the combination of markers SEQ ID No:17 and SEQ ID No:21, the combination of markers SEQ ID No:17 and SEQ ID No:23, the combination of markers SEQ ID No:17 and SEQ ID No:25. In particular, QTL2 causing the invented trait of novel flavour can be identified using the combination of markers SEQ ID No:15, SEQ ID No:17, SEQ ID No:19, SEQ ID No:21, SEQ ID No:23 and SEQ ID No:25, more in particular SEQ ID No:17 and SEQ ID No:15, and most in particular SEQ ID No:17 and SEQ ID No:19.

In the genome of plants grown from seeds of deposit NCIMB 42138 both the markers SEQ ID No:11 and SEQ ID No:13 (full sequence data given in Table 1) are linked to the third QTL, QTL3, that also causes the fruits to have the increased total terpenoid content of the invention, and in particular an increased content of (E)-β-ocimene (FIG. 1C). Although any of these markers or any combination of these markers may be used for identifying QTL3 causing the invented trait of an increased total terpenoid content, and in particular the trait of an increased content of (E)-β-ocimene, marker SEQ ID NO:13 is preferred because it had the highest LOD score in the statistical tests. QTL3 causing the invented trait of an increased total terpenoid content may be identified using the combination of markers SEQ ID No:11 and SEQ ID No:13.

QTL1 is thus present in the genome of the material deposited under deposit number NCIMB 42140, while QTL2 and QTL3 are present in the genome of the material deposited under deposit number NCIMB 42138, and these materials are thus a source of the QTLs that can be used to introduce the trait of an increased total terpenoid content into other pepper plants of the species *Capsicum annuum*. Such plants may be used as a starting point to develop further varieties with the increased total content of terpenoids.

Another possible source of the QTLs of the invention, the introgression fragment on either LG1 (QTL1) or LG10.1 (QTL2 and QTL3), is *Capsicum baccatum*. *Capsicum baccatum*, in particular *Capsicum baccatum* var. *pendulum*, may be used as a source of either of the genomic fragments, the QTLs of the invention, to introduce the trait of an increased total terpenoid content into pepper plants. This is facilitated by the availability of in-fragment markers. Any *Capsicum annuum* pepper plant which may comprise at least one of three QTLs of the invention (QTL1 on LG1 and QTL2 and QTL3 on LG10.1), regardless of the source of these QTLs, is a plant of the invention. A *Capsicum annuum* pepper plant which may comprise at least one of the three QTLs of the invention, wherein this QTL or these QTLs were introduced into this pepper plant from a pepper plant of the invention, for example from a plant grown from seed of deposit NCIMB 42140 for QTL1 and/or NCIMB 42138 for QTL2 and/or QTL3, is therefore the same or equivalent to a *Capsicum annuum* pepper plant which may comprise at least one of the three QTLs of the invention, wherein this QTL or these QTLs were introduced into this pepper plant from a *Capsicum baccatum* plant, in particular a *Capsicum baccatum* var. *pendulum* plant.

In the seeds deposited under deposit number NCIMB 42140, the genetic determinant QTL1 causing the trait of the invention is linked with each of the molecular markers SEQ ID No:1, SEQ ID No:3, SEQ ID No:5, SEQ ID No:7 and SEQ ID No:9. These markers may also be linked to QTL1 that may be comprised in either or both pepper plants that are used as parents in a cross to transfer the trait of an increased total terpenoid content to other plants, but the presence of at least one of the mentioned markers is not essential as long as QTL1 is present.

In the seeds deposited under deposit number NCIMB 42138, the genetic determinant QTL2 causing the trait of the invention is linked with each of the molecular markers SEQ ID No:15, SEQ ID No:17, SEQ ID No:19, SEQ ID No:21, SEQ ID No:23 and SEQ ID No:25. These markers may also be linked to the QTL2, that may be comprised in either or both pepper plants that are used as parents in a cross to transfer the trait of an increased total terpenoids content to other plants, but the presence of at least one of the mentioned markers is not essential as long as QTL2 is present.

In the seeds deposited under deposit number NCIMB 42138, the genetic determinant QTL3 causing the trait of the invention is linked with each of the molecular markers SEQ ID No:11 and SEQ ID No:13. These markers may also be linked to QTL3, that may be comprised in either or both pepper plants that are used as parents in a cross to transfer the trait of an increased (E)-β-Ocimene content to other plants, but the presence of at least one of the mentioned markers is not essential as long as QTL3 is present.

The presence of the increased total terpenoid content trait or phenotype as described herein is a direct indicator that at least one of the three QTLs of the invention, QTL1, QTL2 and QTL3, is present since these QTLs are the genetic information that encode the total terpenoid content trait. Thus, a plant of the invention which has the trait of an increased total terpenoid content as described herein is still a plant of the invention when at least one of the three QTLs, QTL1, QTL2 and QTL3, underlying the phenotype is present therein but the markers no longer are.

Markers are sometimes but not always the genetic cause of a trait. Markers may be located in the gene that causes the trait or are genetically linked to it. They are often used as tools to follow the inheritance of the trait. During breeding, the molecular markers that in the deposited seeds are linked to the genetic determinant may be thus used to assist transfer of the increased total terpenoid content trait to other plants. A skilled breeder would understand that the transfer of the increased total terpenoid content trait into a pepper plant may be monitored by the use of biochemical analysis, or by monitoring and breeding for the presence of molecular markers as described herein (i.e. marker assisted selection), or both. Localization of such markers to specific genomic regions further allows for the use of associated sequences in breeding and for the development of additional linked genetic markers. It will be understood to those skilled in the art that other markers or probes linked to the chromosomal regions of the introgression fragments on LG1 and LG10.1 as identified herein could be employed to identify plants which may comprise at least one of the three QTLs of the invention. Knowledge of the chromosomal regions of the present invention facilitates introgression of the increased total terpenoid content trait of the invention from plants which may comprise at least one of the three QTLs of the invention QTL1, QTL2 and QTL3, such as plants grown from the deposited seeds or *Capsicum baccatum* plants, in particular *Capsicum baccatum* var. *pendulum* plants, into other pepper plants. Linkage blocks of various sizes could be transferred within the scope of this invention as long as at least one chromosomal region confers the increased total terpenoid trait of the invention. Accordingly, it is emphasized that the present invention may be practiced using any molecular markers that genetically map within the identified regions provided that the markers are polymorphic between the parents.

The present invention thus provides a pepper plant (*Capsicum annuum* L.) that produces fruits with an increased total terpenoid content, wherein the pepper plant may comprise at least one of three QTLs, QTL1, QTL2 and QTL3 and wherein QTL1 located on LG1 is as present in the genome of, or obtainable from, *Capsicum baccatum* or pepper plants grown from seeds which were deposited at the NCIMB under accession number NCIMB 42140, and wherein QTL2 and QTL3 located on LG10.1 are as present in the genome of, or obtainable from, *Capsicum baccatum* or pepper plants grown from seeds which were deposited at the NCIMB under accession number NCIMB 42138.

QTL1 is located on LG1 and said QTL is the same as a QTL that is found in the genome of plants grown from seeds of deposit NCIMB 42140 and is linked therein to at least one marker selected from the group consisting of SEQ ID No:1, SEQ ID No:3, SEQ ID No:5, SEQ ID No:7 and SEQ ID No:9.

QTL2 is located on LG10.1 and said QTL is the same as a QTL that is found in the genome of plants grown from seeds of deposit NCIMB 42138 and is linked therein to at least one marker selected from the group of SEQ ID No:15, SEQ ID No:17, SEQ ID No:19, SEQ ID No:21, SEQ ID No:23, SEQ ID No:25.

QTL3 is located on LG10.1 and said QTL is the same as a QTL that is found in the genome of plants grown from seeds of deposit NCIMB 42138 and is linked therein to at least one marker selected from the group of SEQ ID No:11 and SEQ ID No:13.

The present invention relates in particular to plants of the species *Capsicum annuum*. It is understood that a *Capsicum annuum* (pepper) plant is phenotypically identifiable as such, though said plant may contain introgressions from other *Capsicum* species in its genome. The skilled pepper breeder or grower knows how to distinguish *Capsicum annuum* plants and fruits from plants and fruits belonging to other *Capsicum* species.

The pepper plants according to the invention may grow the following fruit types: sweet pepper including pepper, bell pepper, big rectangular pepper, conical pepper, long conical pepper or blocky-type pepper or snack or dolma (=mini blocky). The fruits of the pepper plants according to the invention at maturity may be green, yellow, orange, red, ivory, brown, or purple.

The surprising increase in total terpenoid content, in particular total monoterpenoid content, of pepper fruits of the invention was established by a biochemical analysis. Biochemical profiling of the NILS having QTL1 (NIL36 and NIL47) or QTL2 (NIL45, NIL48 and NIL54) and/or QTL3 (NIL45 and NIL54) introgression (FIG. 1) revealed they had major effects on the terpenoid content of the mature fruits, together affecting at least fifteen different terpenoids (Table 1). QTL1, QTL2 and QTL3 affected only the accumulation of monoterpenes, whereas sesquiterpenes and diterpenes were unaffected by these introgressions. In most cases, the introgressions which may comprise QTL1 and QTL2 resulted in up-regulation of the same compounds, some terpenoids, however, were specifically affected by one of the introgressions. For up-regulating Cineole only the LG1 introgression (QTL1) was effective and for (E)-β-Ocimene the up-regulation was specific for QTL3.

The QTL1 and QTL2 introgressions both resulted in up-regulation of α-Terpinene, γ-Terpinene, Terpinolene, Limonene, Myrcene, Hotrienol, p-Menth-1-en-9-al, Geranic-oxide, Myrcenol, α-Terpineol, Linalool, (E)-Linalooloxide and Linalooloxide. QTL3 resulted in up-regulation of (E)-β-Ocimene.

Surprisingly, the plants of the invention which may comprise at least one of the said two introgressions QTL1 and QTL2 produced fruits in which the level of α-Terpinene, γ-Terpinene, Terpinolene, Limonene, Myrcene, Hotrienol, p-Menth-1-en-9-al, Geranic-oxide, Myrcenol, α-Terpineol, Linalool, (E)-Linalooloxide and Linalooloxide was significantly higher than those of any of the parents (*Capsicum baccatum* var. *pendulum*, SM and GNM) of the crosses that generated them. Moreover, fruits produced by plants having the QTL1 introgression on LG1 of the invention additionally show a significantly higher concentration for the monoterpenoid Cineole, as compared to that of any of the parents (*Capsicum baccatum* var. *pendulum*, SM and GNM) of the crosses that generated them. Fruits produced by plants having the QTL3 introgression on LG10.1 of the invention, on the other hand, only show a significantly higher concentration for the monoterpenoid (E)-β-Ocimene, as compared to that of any of the parents (*Capsicum baccatum* var. *pendulum*, SM and GNM) of the crosses that generated them.

According to the invention fruits of the pepper plant of the invention at least have an increased concentration of one or more terpenoids selected from the group consisting of α-Terpinene, γ-Terpinene, Terpinolene, Limonene, Myrcene, (E)-β-Ocimene, Hotrienol, p-Menth-1-en-9-al, Geranic-oxide, Myrcenol, α-Terpineol, Linalool, Cineole, (E)-Linalooloxide and Linalooloxide. Which one of these terpenoids is up-regulated depends on the QTL that is present. The increase is as compared to pepper fruits of a similar ripening stage from isogenic plants not carrying that particular QTL.

The (additive) effect that each QTL of the invention independently has on the terpenoid content in the fruits of the plant which may comprise said QTL may be determined by measuring the volatile compound abundance, also called intensity, level or concentration, of terpenoids, in particular monoterpenoids, in particular the monoterpenoids α-Terpinene, γ-Terpinene, Terpinolene, Limonene, Myrcene, (E)-β-Ocimene, Hotrienol, p-Menth-1-en-9-al, Geranic-oxide, Myrcenol, α-Terpineol, Linalool, Cineole, (E)-Linalooloxide and Linalooloxide and comparing the measured abundance to that measured in pepper fruits of a similar ripening stage from isogenic plants not carrying that specific QTL of the invention.

As the ripening stage affects the biochemical characteristics of pepper fruits, it is understood that comparisons between pepper plants carrying at least one of the three QTLs of the invention with pepper plants not carrying one or any of these QTLs should be made between plants of a similar fruit ripening stage, for example at a fully mature and ripe stage in which the pepper fruits are 95-100% colored, as mentioned in example 2.

An increased concentration is defined herein as the volatile compound abundance, also called intensity, for a specific volatile compound measured on a sample of fruits of plants of the invention carrying one or more QTLs of the invention being, in order of increased preference, at least 1.5 times higher, 2 times higher, 3 times higher, 4 times higher, 5 times higher, 6 times higher, 7 times higher, 10 times higher, 15 times higher, 20 times higher, 25 times higher, 30 times higher, 35 times higher, 40 times higher, 45 times higher, 50 times higher than the average peak intensity for fruits of a similar ripening stage from an isogenic pepper plant not comprising said QTL included in the same experiment.

Suitably the volatile compound abundance for a specific volatile compound measured on a sample of fruits of plants of the invention carrying one or more QTLs of the invention is at maximum 200 times higher than the volatile compound abundance for fruits of a similar ripening stage from an isogenic pepper plant not comprising said QTL included in the same GC-MS experiment. This corresponds to an increase of, in order of increased preference, at least 0.58 times, at least 1.0 times, at least 1.58 times, at least 2.0 times, at least 2.32 times, at least 2.58 times, at least 2.81 times, at least 3.32 times, at least 3.91 times, at least 4.32 times, at least 4.64 times, at least 4.91 times, at least 5.13 times, at least 5.32 times, at least 5.49 times, at least 5.46 times, and at maximum 7.64 times when peak intensity values are given as log 2 transformed peak intensity values.

Fruits of the invention that carry QTL1 have an increased concentration of one or more terpenoids selected from the group consisting of α-Terpinene, γ-Terpinene, Terpinolene, Limonene, Myrcene, Hotrienol, p-Menth-1-en-9-al, Geranic-oxide, Myrcenol, α-Terpineol, Linalool, Cineole, (E)-Linalooloxide and Linalooloxide, as compared to pepper fruits of a similar ripening stage from isogenic plants not carrying QTL1.

Preferably, fruits of the pepper plant of the invention, which may comprise QTL1, have an increased concentration of one or more terpenoids selected from the group consisting of p-Menth-1-en-9-al and Cineole, and optionally have an increased concentration of one or more terpenoids selected from the group consisting of α-Terpinene, γ-Terpinene, Terpinolene, Limonene, Myrcene, Hotrienol, Geranic-oxide, Myrcenol, α-Terpineol, Linalool, (E)-Linalooloxide and Linalooloxide, as compared to pepper fruits of a similar ripening stage from isogenic plants not carrying QTL1.

Fruits carrying QTL1 more preferably have an increased concentration of all these 14 terpenoids.

Fruits of the pepper plant of the invention, which may comprise QTL2, have an increased concentration of one or more terpenoids selected from the group consisting of α-Terpinene, γ-Terpinene, Terpinolene, Limonene, Myrcene, Hotrienol, p-Menth-1-en-9-al, Geranic-oxide, Myrcenol, α-Terpineol, Linalool, (E)-Linalooloxide and Linalooloxide, as compared to pepper fruits of a similar ripening stage from isogenic plants not carrying the said QTL.

Preferably, fruits of the pepper plant of the invention, which may comprise QTL2, have an increased concentration of one or more terpenoids selected from the group consisting of Terpinolene, Limonene, p-Menth-1-en-9-al, Geranic-oxide, Myrcenol, α-Terpineol, (E)-Linalooloxide and Linalooloxide, and optionally have an increased concentration of one or more terpenoids selected from the group consisting of α-Terpinene, γ-Terpinene, Myrcene, Hotrienol and Linalool, as compared to pepper fruits of a similar ripening stage from isogenic plants not carrying QTL2.

Fruits carrying QTL2 more preferably have an increased concentration of all these 13 terpenoids.

Fruits of the pepper plant of the invention, which may comprise QTL3 has an increased concentration of (E)-β-Ocimene.

Fruits of plants carrying the combination of QTL1 and QTL2 preferably show an increase in all 14 terpenoids mentioned above for QTL1. Fruits that also carry QTL3 are preferably increased in all 14 terpenoids plus (E)-β-Ocimene. When a plant has both QTL1 and QTL3 it preferably shows an increase in all 15 terpenoids. When QTL2 and QTL3 are combined the plant has 14 up-regulated terpenoids.

Preferably, fruits of the pepper plant of the invention, which may comprise QTL1, have an increased concentration of p-Menth-1-en-9-al and Cineole, and optionally have an increased concentration of α-Terpinene, γ-Terpinene, Terpinolene, Limonene, Myrcene, Hotrienol, Geranic-oxide, Myrcenol, α-Terpineol, Linalool, (E)-Linalooloxide and Linalooloxide, as compared to pepper fruits of a similar ripening stage from isogenic plants not carrying the said QTL.

In a further embodiment, fruits of the pepper plant of the invention, which may comprise QTL2, have an increased concentration of Terpinolene, Limonene, p-Menth-1-en-9-al, Geranic-oxide, Myrcenol, α-Terpineol, (E)-Linalooloxide and Linalooloxide, and optionally have an increased concentration of α-Terpinene, γ-Terpinene, Myrcene, Hotrienol and Linalool, as compared to pepper fruits of a similar ripening stage from isogenic plants not carrying the said QTL.

The up-regulation of terpenoids is strongest when determined in the fruits of plants that have one or more of QTL1, QTL2 and QTL3 in a homozygous state. In the fruits of plants that have one or more of QTL1, QTL2 and QTL3 in a heterozygous state, the concentrations for the corresponding monoterpenoids are intermediate between those of pepper fruits at a similar ripening stage of isogenic plants without the specific QTL(s) and fruits of plants wherein the specific QTL(s) of the invention is(are) present in a homozygous state.

The present invention furthermore covers a pepper plant producing fruits with an increased total content of terpenoids, caused by at least one of QTL1, QTL2 and QTL3, and wherein that one QTL, or those two QTLs, or those three QTLs can be present both homozygously and heterozygously.

One of the technical effects of the trait of the invention was established in a spider mite (*Tetranychus urticae*) development test. An analysis of egg deposition of spider mites on leaf discs of the NILS having a QTL1 (NIL36 and NIL47) or QTL2 (NIL45, NIL48 and NIL54) and/or QTL3 (NIL45 and NIL54) introgression (FIG. 1) revealed they had a significantly lower spider mite egg deposition compared to recurrent parent GMN, three randomly selected NILS not carrying any QTL of the invention and *Capsicum baccatum* var. *pendulum* PEN45 (FIG. 3). The decrease in spider mite egg deposition compared to plants not carrying any QTL of the invention was most clear in plants of the invention carrying both QTL2 and QTL3. Plants of the invention thus have a higher level of resistance to spider mites than plants not carrying any of the QTLs of the invention.

The invention thus also relates to a pepper plant (*Capsicum annuum* L.) that produces fruits with an increased total content of terpenoids and demonstrating an increased level of spider mite (*Tetranychus urticae*) resistance as a result of the presence in the genome of the pepper plant of at least one QTL selected from QTL1, QTL2 and QTL3, wherein:
QTL1 is the same or similar to the QTL that in the genome of plants grown from seeds of deposit NCIMB 42140 is located on LG1 and is linked therein to at least one marker selected from the group consisting of SEQ. No:1, SEQ ID No:3, SEQ ID No:5, SEQ ID No:7 and SEQ ID No:9;

QTL2 is the same or similar to the QTL that in the genome of plants grown from seeds of deposit NCIMB 42138 is located on LG10.1 and is linked therein to at least one marker selected from the group of SEQ ID No:15, SEQ ID No:17, SEQ ID No:19, SEQ ID No:21, SEQ ID No:23 and SEQ ID No:25; and QTL3 is the same or similar to the QTL that in the genome of plants grown from seeds of deposit NCIMB 42138 is located on LG10.1 and is linked therein to at least one marker selected from the group of SEQ ID No:11 and SEQ ID No:13.

In a further embodiment, the invention provides a pepper plant (*Capsicum annuum* L.) that produces fruits with an increased total content of terpenoids and demonstrating an increased level of anthracnose resistance as a result of the presence in the genome of the pepper plant of at least one QTL selected from QTL1, QTL2 and QTL3 as defined above.

In another embodiment, the invention provides a pepper plant (*Capsicum annuum* L.) that produces fruits with an increased total content of terpenoids and demonstrating an increased level of indirect defence as a result of the presence in the genome of the pepper plant of at least one QTL selected from QTL1, QTL2 and QTL3 as defined above.

The invention relates also to seed of pepper plants of the invention and to other parts of the plant that are suitable for sexual reproduction. Such plant parts can be selected from the group consisting of microspores, pollen, ovaries, ovules, embryo sacs and egg cells.

Additionally, the invention also relates to parts of the pepper plants of the invention that are suitable for vegetative reproduction, for example tissue culture, cuttings, roots, stems, cells and protoplasts. Tissue culture can be grown from leaves, pollen embryos, cotyledon, hypocotyls, meristematic cells, roots, anthers, flowers, seeds and stems.

In this application any plant, seed or propagation material may comprise one, two or three of the QTLs disclosed herein. Each QTL can be present either in homozygous or heterozygous state. This leads to the following possible combinations.

QTL1, QTL2 and QTL3, that in the fruits of the plant that can be grown from the seed causes the trait of an increased total terpenoid content.

The invention furthermore relates to hybrid seed and to a method of producing hybrid seeds which may comprise crossing a first parent plant with a second parent plant and harvesting the resulting hybrid seed. Such hybrid seed may comprise one or more of QTL1, QTL2 and QTL3 of the invention. In order for all the hybrid seed to carry the trait of the invention homozygously, both parents need to be homozygous for all of its QTLs. In that case both parents thus carry at least one of the QTLs of the invention. They need not necessarily be uniform for other traits.

Beside the seed of a pepper plant, the invention also covers the progeny derived from a pepper plant producing fruits with an increased total content of terpenoids. Such progeny may be produced by sexual and vegetative reproduction of a plant of the invention or a progeny plant thereof. The progeny carries at least one of QTL1, QTL2 and QTL3 of the invention. In addition to this, the plant may be modified in one or more other characteristics. Such additional modifications are for example effected by crossing and selecting, mutagenesis or by transformation with a transgene.

As used herein the word "progeny" is intended to mean the offspring or the first and all further descendants from a cross with a plant of the invention that shows the trait of the invention and carries at least one of QTL1, QTL2 and QTL3 of the invention. Progeny of the invention may comprise descendants of any cross with a plant of the invention that carries any of the QTLs of the invention causing the increased terpenoid content trait of the invention. Such progeny is for example obtainable by crossing a first pepper plant with a second pepper plant, wherein one of the plants was grown from seeds of which a representative sample was deposited under accession number NCIMB 42140 and NCIMB 42138, but may also be the progeny of any other pepper plant carrying at least one of the QTLs of the invention, wherein QTL1 is as present in NCIMB 42140 and/or QTL2 and QTL3 as present in NCIMB 42138.

Furthermore, the current invention also covers progeny of a pepper plant of the current invention or progeny of pepper plants grown from seeds derived from plants of the current

| QTL | | | | | | | | |
|---|---|---|---|---|---|---|---|---|
| 1 | He* | Ho** | | | | | | |
| 2 | He | Ho | | | | | | |
| 3 | He | Ho | | | | | | |
| 1 + 2 | He + He | Ho + Ho | He + Ho | Ho + He | | | | |
| 1 + 3 | He + He | Ho + Ho | He + Ho | Ho + He | | | | |
| 2 + 3 | He + He | Ho + Ho | He + Ho | Ho + He | | | | |
| 1 + 2 + 3 | He + He + He | Ho + Ho + Ho | He + He + Ho | Ho + He + Ho | He + He + Ho | Ho + He + He | He + Ho + Ho | Ho + Ho + He |

*Heterozygous
**Homozygous

The invention further relates to seed of a pepper plant producing fruits with an increased total terpenoid content, wherein the genome of the pepper seed may comprise at least one of QTL1, QTL2 and QTL3, that in the fruits of the plant that can be grown from the seed causes the trait of an increased total terpenoid content.

The invention also relates to seed that is capable of growing into a pepper plant of the invention, wherein the genome of the pepper seed may comprise at least one of invention, wherein the progeny of the plant may comprise at least one of the QTLs of the invention. The increased terpenoid content trait thus has a genetic basis in the genome of a *Capsicum annuum* plant, and for example by using the biochemical analysis as described in Example 3 *Capsicum annuum* plants may be identified as being plants of the invention.

A pepper plant of the invention, producing fruits with an increased total content of terpenoids that is caused by at least one of the QTLs of the invention is obtainable by crossing a first pepper plant not having any QTL of the invention, with a second pepper plant having at least one of the QTLs of the invention, or by introgression of at least one of the QTLs of the invention into the first pepper plant from the second pepper plant, and selecting plants that produce fruits which have at least one of the said QTLs and/or the increased total terpenoid content and/or an increased concentration of α-Terpinene and/or γ-Terpinene and/or Terpinolene and/or Limonene and/or Myrcene and/or (E)-β-Ocimene and/or Hotrienol and/or p-Menth-1-en-9-al and/or Geranic-oxide and/or Myrcenol and/or α-Terpineol and/or Linalool and/or Cineole and/or (E)-Linalooloxide and/or Linalooloxide compared to fruits of a similar ripening stage from an isogenic pepper plant not comprising said QTL or said QTLs.

Propagation material derived from a pepper plant of the invention or from pepper seeds from a pepper plant of the invention, is also included in the present invention, wherein the propagation material may comprise at least one of the QTLs of the invention that cause the increased total terpenoid content, and the QTL is or the QTLs are preferably present in a homozygous state.

The invention also refers to propagation material capable of growing into a pepper plant of the invention, wherein the propagation material may comprise at least one of the QTLs of the invention that cause the increased total terpenoid content, and the QTL is or the QTLs are preferably present in a homozygous state.

The said propagation material, derived from the pepper plant of the invention as well as propagation material capable of growing into a plant of the invention is for example selected from the group consisting of callus, microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds and stems or parts or tissue culture thereof.

The invention further relates to a cell of a pepper plant having an increased total terpenoid content, which cell may comprise at least one of QTL1, QTL2 and QTL3, wherein QTL1 is as present in the genome of a pepper plant grown from seeds of which a representative sample was deposited with the NCIMB under accession number NCIMB 42140 and QTL2 and QTL3 are as present in the genome of a pepper plant grown from seeds of which a representative sample was deposited with the NCIMB under accession number NCIMB 42138. The said cell thus may comprise the genetic information which is substantially identical, preferably completely identical to the genetic information encoding the said increased total content of terpenoids trait of the pepper plant grown from seeds of which a representative sample was deposited under NCIMB accession number NCIMB 42140 and NCIMB 42138. The genetic information may comprise QTL1, QTL2 and QTL3 either alone or in any combination.

Preferably, the cell of the invention is a part of a plant or plant part, but the cell may also be in isolated form.

In one embodiment, the invention relates to the use of seeds with NCIMB accession number NCIMB 42140 and/or seeds with NCIMB accession number NCIMB 42138, for transferring at least one of the QTLs of the invention into another pepper plant.

In another embodiment, the invention relates to the use of a pepper plant having one or more of QTL1, QTL2 and QTL3 as a crop.

The invention also relates to the use of a pepper plant having one or more of QTL1, QTL2 and QTL3 as a source of seed.

In yet another embodiment, the invention relates to the use of a pepper plant having one or more of QTL1, QTL2 and QTL3 as a source of propagating material.

Further, the invention relates to the use of a pepper plant having one or more of QTL1, QTL2 and QTL3 for consumption.

In another embodiment, the invention relates to the use of a pepper plant or a *Capsicum baccatum* plant having one or more of QTL1, QTL2 and QTL3 for conferring the trait of invention higher total terpenoid content to a pepper plant.

In yet another embodiment, the invention relates to the use of a pepper plant, as a recipient of at least one of QTL1, QTL2 and QTL3.

QTL1, QTL2 and QTL3 are as present in and obtainable from a *Capsicum baccatum* or a pepper plant, in particular a pepper plant grown from seed with NCIMB accession number NCIMB 42140 for QTL1 and NCIMB 42138 for QTL2 and QTL3.

The current invention also relates to a pepper fruit, or parts thereof, harvested from a pepper plant of the invention, producing fruits with an increased total content of terpenoids and which may comprise at least one of QTL1, QTL2 and QTL3. Naturally this also relates to any food product or processed food product made of said pepper fruit. Such food product is for example selected from powders, soups, sauces, salsas, condiments, pastas, curries, pastries, sweets and salads. Such food product will usually be pre-packed and is intended for sale in a supermarket. The invention thus also relates to the use of pepper fruits harvested from a pepper plant of the invention, or parts thereof, in the preparation of food products, in particular sauces, salads, pies, soups and pastas.

A pepper plant of the invention could also be used as germplasm in a breeding program for the development of other pepper plants that may comprise at least one of QTL1, QTL2 and QTL3 that causes the increased total terpenoid content. This kind of use is also covered by the current invention.

Moreover, the invention relates to a nucleic acid or a part thereof, optionally in isolated form, which causes an increased total content of terpenoids in pepper fruits, which nucleic acid originates from LG1 and is in the genome of plants grown from seeds of deposit NCIMB 42140 linked thereon to at least one of the molecular markers selected from the group of SEQ ID NO:1, SEQ ID No:3, SEQ ID No:5, SEQ ID No:7 and SEQ ID NO:9 or originates from LG10.1 and is in the genome of plants grown from seeds of deposit NCIMB 42138 linked thereon to at least one of the molecular markers selected from the group of SEQ ID NO:11, SEQ ID No:13, SEQ ID No:15, SEQ ID No:17, SEQ ID No:19, SEQ ID NO:21, SEQ ID No:23 and SEQ ID No:25. A person skilled in the art would be able to isolate the nucleic acid causing the increased total content of terpenoids trait of the invention or a part thereof from the genome of a pepper plant of the invention, and use it to create new molecular markers that are linked with one or both of the QTLs and with the trait of the invention.

The present invention also relates to the use of a molecular marker, wherein the molecular marker selected from the group consisting of SEQ ID No:1, SEQ ID No:3, SEQ ID No:5, SEQ ID No:7, SEQ ID No:9, SEQ ID No:11, SEQ ID No:13, SEQ ID No:15, SEQ ID No:17, SEQ ID No:19, SEQ ID No:21, SEQ ID No:23 and SEQ ID No:25 to identify QTL1 and/or QTL2 and/or QTL3, or to develop pepper plants producing fruits that have an increased total content of terpenoids.

The present invention further relates to the use of said molecular marker to identify or develop other markers linked to QTL1 and/or QTL2 and/or QTL3 that cause the increased total content of terpenoids.

In order to establish the presence of QTL1 of the invention in the genome of a seed or plant at least one molecular marker is necessary but any combination of the molecular markers according to SEQ ID No:1, SEQ ID No:3, SEQ ID No:5, SEQ ID No:7 and SEQ ID No:9 may be used. In order to establish the presence of QTL2 of the invention in the genome of a seed or plant at least one molecular marker is necessary but any combination of the molecular markers according to SEQ ID No:15, SEQ ID No:17, SEQ ID No:19, SEQ ID No:21, SEQ ID No:23 and SEQ ID No:25 may be used. QTL3 can be identified with the markers according to SEQ ID No:11 and/or SEQ ID No:13.

Genotyping a population of plants segregating for the increased total terpenoid content trait of the invention can be done using at least one molecular marker set selected from the group consisting of SEQ ID No:1 plus SEQ ID No:2, SEQ ID No:3 plus SEQ ID No:4, SEQ ID No:5 plus SEQ ID No:6, SEQ ID No:7 plus SEQ ID No:8 and SEQ ID No:9 plus SEQ ID No:10, and/or using at least one molecular marker set selected from the group consisting of, SEQ ID No:15 plus SEQ ID No:16, SEQ ID No:17 plus SEQ ID No:18, SEQ ID No:19 plus SEQ ID No:20, SEQ ID No:21 plus SEQ ID No:22, SEQ ID No:23 plus SEQ ID No:24 and SEQ ID No:25 plus SEQ ID No:26 and/or by using at least one molecular marker set selected from SEQ ID No:11 plus SEQ ID No:12 and SEQ ID No:13 plus SEQ ID No:14. The presence of the increased total content of terpenoids trait of the invention can also be determined phenotypically by a biochemical assay in either generation of an introgression process.

In one aspect the invention relates to a method for production of a pepper plant which has the trait of an increased total content of terpenoids, which may comprise
a) crossing a plant which may comprise at least one of QTL1, QTL2 and QTL3 with another plant;
b) selecting plants that have the trait in the next generation;
c) optionally performing one or more additional rounds of selfing or crossing, and subsequently selecting, for a plant which may comprise/show the trait of the invention.

Selecting plants that have the trait of an increased total content of terpenoids can be done molecularly using molecular markers linked to the trait as described herein and/or phenotypically in the F1 or F2 or any further generation.

In one aspect, the invention relates to a method for production of a pepper plant which has the trait of increased total terpenoid content, which may comprise
a) crossing a plant which may comprise at least one of QTL1, QTL2 and QTL3 with another plant;
b) optionally backcrossing the resulting F1 with the preferred parent;
c) selecting for plants that have the trait in the next generation;
d) optionally performing one or more additional rounds of selfing or crossing, and subsequently selecting, for a plant which may comprise the trait.

The invention additionally provides a method of introducing another desired trait into a pepper plant which has the trait of an increased total content of terpenoids, which may comprise:

a) crossing a plant which may comprise at least one of QTL1, QTL2 and QTL3 with a second pepper plant that may comprise a further desired trait to produce F1 progeny;
b) selecting in the F1 progeny plants that may comprise said trait of an increased total content of terpenoids and the desired trait;
c) crossing the selected F1 progeny plants with either parent, to produce backcross progeny;
d) selecting backcross progeny plants which may comprise the desired trait and the trait of an increased total content of terpenoids; and
e) optionally repeating steps c) and d) one or more times in succession to produce selected fourth or higher backcross progeny that may comprise the desired trait and the trait of an increased total content of terpenoids.

The invention includes a pepper plant produced by this method.

Suitably at least one of the parent plants in the above described methods is a plant grown from seeds of which a representative sample was deposited under deposit number NCIMB 42140 or NCIMB 42138.

The word "trait" in the context of this application refers to the phenotype of the plant. In particular, the word "trait" refers to the trait of the invention, more in particular to the trait of pepper fruits with an increased total content of terpenoids. The term "QTL" (i.e. "quantitative trait locus") is used for the genetic information in the genome of the plant that causes the increased total terpenoid content trait of the invention. When a plant shows the increased total terpenoid content trait of the invention, its genome may comprise at least one of QTL1, QTL2 and QTL3, causing the trait of the invention. The plant thus has at least one of the QTLs of the invention. In the present invention the QTLs of the invention are: QTL1, an introgression from *C. baccatum* on Linkage Group 1 (LG1); QTL2, an introgression from *C. baccatum* on Linkage Group 10.1 (LG10.1) and QTL3, a further introgression from *C. baccatum* on Linkage Group 10.1 (LG10.1).

It is clear that the parent that provides the trait of the invention is not necessarily a plant grown directly from the deposited seeds. The parent may also be a progeny plant from the deposited seed, obtained by for example selfing or crossing, or a progeny plant from seeds that are identified to have the trait of the invention by other means.

In one embodiment selection for plants having the trait of an increased total content of terpenoids is done in the F1 or any further generation by using any or any combination of the markers according to SEQ ID No:1, SEQ ID No:3, SEQ ID No:5, SEQ ID No:7, SEQ ID No:9, SEQ ID No:11, SEQ ID No:13, SEQ ID No:15, SEQ ID No:17, SEQ ID No:19, SEQ ID No:21, SEQ ID No:23 and SEQ ID No:25. In another aspect, selection for the trait of the invention is started in the F2 of a cross or alternatively of a backcross. Selection of plants in the F2 can be done phenotypically as well as by using the said marker(s) which directly or indirectly detect(s) one or more of QTL1, QTL2 and QTL3 of the invention underlying the trait. Phenotypic selection can suitably be done by determining the biochemical profile of the pepper fruits.

In one embodiment selection for plants having the trait of an increased total terpenoid content is started in the F3 or a later generation.

In one embodiment the plant which may comprise the one or more of QTL1, QTL2 and QTL3 of the invention is a plant of an inbred line, a hybrid, a doubled haploid, or of a segregating population.

The invention further provides a method for the production of a pepper plant having the trait of an increased total content of terpenoids by using a doubled haploid generation technique to generate a doubled haploid line which may comprise said trait.

The invention furthermore relates to hybrid seed that can be grown into a plant having the trait of an increased total content of terpenoids and to a method for producing such hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid pepper plant that has the trait of an increased total content of terpenoids, which may comprise crossing a first parent pepper plant with a second parent pepper plant and harvesting the resultant hybrid seed, of which the first parent plant and/or the second parent plant has the trait of an increased total content of terpenoids, and growing said hybrid seeds into hybrid plants having the trait of an increased total content of terpenoids.

The invention also relates to a method for the production of a pepper plant having the trait of an increased total content of terpenoids. This is suitably done by using a seed that may comprise at least one of QTL1, QTL2 and QTL3 in its genome that leads to the trait of an increased total content of terpenoids for growing the said pepper plant. The seeds are suitably seeds of which a representative sample was deposited with the NCIMB under deposit number NCIMB 42140 or NCIMB 42138.

The invention also relates to a method for seed production which may comprise growing pepper plants from seeds of a pepper plant having the trait of an increased total content of terpenoids, allowing the plants to produce seeds, and harvesting those seeds. Production of the seeds is suitably done by crossing or selfing. The pepper plant having the trait of an increased total content of terpenoids is suitably grown from seed that may comprise at least one of QTL1, QTL2 and QTL3 in its genome. A representative sample of such seeds was deposited with the NCIMB under deposit number NCIMB 42140 and/or NCIMB 42138

In one embodiment, the invention relates to a method for the production of a pepper plant having the trait of an increased total content of terpenoids by using tissue culture.

The invention furthermore relates to a method for the production of a pepper plant having the trait of an increased total content of terpenoids by using vegetative reproduction.

In one embodiment, the invention relates to a method for the production of a pepper plant having the trait of an increased total content of terpenoids by using a method for genetic modification to introgress one or more of QTL1, QTL2 and QTL3 into the pepper plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

In one embodiment, the source from which the genetic information is acquired, in particular QTL1, QTL2 and QTL3 of the invention, is formed by a plant grown from the deposited seeds, or by sexual or vegetative descendants thereof.

The invention also relates to a breeding method for the development of pepper plants that have the trait of an increased total content of terpenoids wherein germplasm which may comprise at least one of QTL1, QTL2 and QTL3 is used. The germplasm is constituted by all inherited characteristics of an organism and according to the invention encompasses at least the increased total terpenoid content trait of the invention.

In a further embodiment the invention relates to a method for the production of a pepper plant having the trait of an increased total content of terpenoids wherein progeny or propagation material of a plant which may comprise the QTL or QTLs of the invention conferring said trait is used as a source to introgress the said trait into another pepper plant.

Furthermore, the invention relates to three so-called increased total terpenoid genes that lead to a pepper plant having the increased total terpenoid content trait of the invention, and which genes are as present in the genome of plants of which a representative sample was deposited with the NCIMB under deposit number NCIMB 42140 (gene on LG1) and NCIMB 42138 (two genes on LG10.1). The skilled breeder knows how to use such plant as a source of one (NCIMB 42140) or two (NCIMB 42138) of the three genes for introgressing the increased total terpenoid content trait or phenotype into a plant.

The invention also relates to the use of at least one of QTL1, QTL2 and QTL3, that lead to a pepper plant producing fruits having the trait of an increased total terpenoid content, for producing a plant which has the trait of an increased total terpenoid content, in particular a pepper plant which has the increased total terpenoid trait, which QTL1 is as present in the genome of plants of which a representative sample was deposited under deposit number NCIMB 42140 and which QTL2 and QTL3 are as present in the genome of plants of which a representative sample was deposited under deposit number NCIMB 42138.

According to another aspect thereof the invention relates to a non-naturally occurring plant producing fruits having an increased total terpenoid content, and which increased total terpenoid content is the result of the presence in the genome of the plant of at least one of QTL1, QTL2 and QTL3. Representative seed which may comprise QTL1, was deposited with the NCIMB under deposit number NCIMB 42140, and representative seed which may comprise QTL2 and QTL3, was deposited with the NCIMB under deposit number NCIMB 42138. The non-naturally occurring plant is in particular a mutant plant.

If not explicitly mentioned, in the above described methods, seeds and plants the trait of an increased total content of terpenoids is caused by the presence in the genome of the pepper plant involved of at least one of QTL1, QTL2 and QTL3. Representative seed of said plant which may comprise QTL1, was deposited with the NCIMB under deposit number NCIMB 42140, and representative seed of said plant which may comprise QTL2 and QTL3, was deposited with the NCIMB under deposit number NCIMB 42138.

In this application references to an increase in the total content of terpenoids preferably relate to an increase in the total content of monoterpenoids.

Terpenes and terpenoids are naturally occurring hydrocarbons based on combinations of the isoprene unit. In this application the terms terpenoids and terpenes are used interchangeably and encompass all compounds that may be grouped under these terms.

Introgression as used in this application is intended to mean introduction of a trait into a plant not carrying the trait by means of crossing and selecting.

The term 'nucleic acid' is used for a macromolecule, a DNA or RNA molecule, containing the genetic information that causes the trait of the invention. When a plant shows the phenotypic trait of the invention, its genome may comprise the nucleic acid(s) causing that trait. The plant thus has the nucleic acid(s) of the invention. In the present invention the nucleic acid is part of QTL1 introgressed from *C. baccatum* on Linkage Group 1 (LG1) or is part of, or encompasses, QTL2 and/or QTL3 introgressed from *C. baccatum* on Linkage Group 10.1 (LG10.1).

The invention provides preferably a pepper plant having the trait of producing fruits with an increased total content of terpenoids, which plant is obtainable by any of the methods described herein and/or familiar to the skilled person.

In the absence of molecular markers, or in the instance that recombination between a QTL and its marker(s) has taken place so that the marker(s) is(are) not predictive anymore, it can be determined by an allelism test whether in a plant that has an increased total content of terpenoids the said trait is caused by genetic information that is the same or similar to one or more of QTL1, QTL2 and QTL3 of the invention. To perform an allelism test, a tester plant which is homozygous for one or more of QTL1, QTL2 and QTL3 is crossed with material to be tested that is also homozygous for the genetic information underlying the increased terpenoid trait. When no segregation for the trait to be observed is present in the F2 of the cross, the unknown genetic information has been proven to be equivalent or the same as the one or more QTLs of the invention as in the genome of the tester plant. Preferably, the tester plant is homozygous for all three QTLs.

Marker Information

TABLE 1

Molecular SNP markers.

| marker name | LG | position (cM) | Sequence marker |
|---|---|---|---|
| SEQ ID No: 1 | 1 | 20.17 | GTGCAGGCACCCCTGGGACCTGATATCTCAAGTCCACAGCTTGTTGCTGCTGTTGCTAATTCTGGTGCTCTTGGTTTTCTCA |
| SEQ ID No: 2 | 1 | 20.17 | GTGCAGGCACCCCTGGGACCTGATATCTCAAGTCCACATCTTGTTGCTGCTGTTGCTAATTCTGGTGCTCTTGGTTTTCTCA |
| SEQ ID No: 3 | 1 | 21.13 | GTTGATTATCCTTGCAAGCACTGAAACTGATGGCCCTGCCACCACTTGTGCCCTTATAAGTGCCGGATAGGGATCTGTTATCATCCCATTTGTT |
| SEQ ID No: 4 | 1 | 21.13 | GTTGATTATCCTTGCAAGCACTGAAACTGATGGCCCTGACACCACTTGTGCCCTTATAAGTGCCGGATAGGGATCTGTTATCATCCCATTTGTT |
| SEQ ID No: 5 | 1 | 23.64 | TGATGCTCATACACACTCTCCACGAGTTGAGGAATCAACTTACTCAGGAAGTGCAAAGCGATTTGTAAGCGTCTTGTCTAAGCCGGTGAACAACAAAC |
| SEQ ID No: 6 | 1 | 23.64 | TGATGCTCATACACACTCTCCACGAGTTGAGGAATCAACTTACTCAGGAAGTTCAAAGCGATTTGTAAGCGTCTTGTCTAAGCCGGTGAACAACAAAC |
| SEQ ID No: 7 | 1 | 24.65 | CGCATACCTTGCCCCTTCTTTGGGGTCTGSTGTTGTTCCAACAGAAACAACCTCCAGATCCTGATTCATATCCCCTGCAG |
| SEQ ID No: 8 | 1 | 24.65 | CGCATACCTTGCCCCTTCTTTGGGGTCTGSTGTTGTTCCAACAGAAACAACCTCCGGATCCTGATTCATATCCCCTGCAG |

TABLE 1-continued

Molecular SNP markers.

| marker name | LG | position (cM) | Sequence marker |
|---|---|---|---|
| SEQ ID No: 9 | 1 | 24.82 | TTTGTAAGGATTTCCCAAGATCATTCATCAAAGCTATTCTCCCCAAACAAACGACTTCGTTCCAACTTGGGTTCCACCAATTTCAGTTGGGGTTGTTT |
| SEQ ID No: 10 | 1 | 24.82 | TTTGTAAGGATTTCCCAAGATCATTCATCAAAGCTATTCTCCCCAAACAAACAACTTCGTTCCAACTTGGGTTCCACCAATTTCAGTTGGGGTTGTTT |
| SEQ ID No: 11 | 10.1 | 0 | GCTCCTAGTTCCACAGGAGCCGATGGAGAGGCACATAACTACTTTGGTGAAGCAGAATTTGCAAGATGTAACGGCTGCTGAATTTAAAATGTTCATGGAC |
| SEQ ID No: 12 | 10.1 | 0 | GCTCCTAGTTCCACAGGAGCCGATGGAGAGGCACATAACTACTTTGGTGAAGAAGAATTTGCAAGATGTAACGGCTGCTGAATTTAAAATGTTCATGGAC |
| SEQ ID No: 13 | 10.1 | 6.32 | GATGCAAACAACMARRAAARRAMAAAAWTCCGTTCACGAGCAAAGAACCTCGTGAAGCAACTCTAAATAAGCTTTACCTGATAGGTTGGGAGCCCAACATCTCACCACAAAGATCCAAC |
| SEQ ID No: 14 | 10.1 | 6.23 | GATGCAAACAACMARRAAARRAMAAAAWTCCGTTCACGAGCAAAGAACTTCGTGAAGCAACTCTAAATAAGCTTTACCTGATAGGTTGGGAGCCCAACATCTCACCACAAAGATCCAAC |
| SEQ ID No: 15 | 10.1 | 15.55 | GAGCATCTTATTTGAAGACCAAGAAGGGGAAAAAGGGTTTCAAAGGTGGCAAAAAGGGCAGGGGAAATGGAAATGGAAAGGGAAGGAAAGGCTGATTGCAGCTTATC |
| SEQ ID No: 16 | 10.1 | 15.55 | GAGCATCTTATTTGAAGACCAAGAAGGGGAAAAAGGGTTTCAAAGGTGGCAAAAAAGGCAGGGGAAATGGAAATGGAAAGGGAAGGAAAGGCTGATTGCAGCTTATC |
| SEQ ID No: 17 | 10.1 | 16.56 | GAAAGGGACAATGATGACAACGGTAGTGCTTTTTTACYRASTGATGATGAGACTTATGCAAAGCCTTGACCAGGGAGTCCTTTAGTTCCACCTTACTTGTTTWTTGTTTTATTTGTGG |
| SEQ ID No: 18 | 10.1 | 16.56 | GAAAGGGACAATGATGACAACGGTAGTGCTTTTTTACYRASTGATGATGAGACTTATACAAAGCCTTGACCAGGGAGTCCTTTAGTTCCACCTTACTTGTTTWTTGTTTTATTTGTGG |
| SEQ ID No: 19 | 10.1 | 17.03 | CCATCTGAAATCCTCCAACAAGAATACAACATGACACTCAAGGCTCAAGCTATACTAGCAAAGTTGTGGTCATTATAACGTGCATTACAAGATGGCCAAAAAGCTC |
| SEQ ID No: 20 | 10.1 | 17.03 | CCATCTGAAATCCTCCAACAAGAATACAACATGACACTCAAGGCTCAAGCTGTACTAGCAAAGTTGTGGTCATTATAACGTGCATTACAAGATGGCCAAAAAGCTC |

TABLE 1-continued

Molecular SNP markers.

| marker name | LG | position (cM) | Sequence marker |
|---|---|---|---|
| SEQ ID No: 21 | 10.1 | 17.11 | TCCCCAAGCTTATAAACACTTCGT CAAGAGCTGCCACCTCATCGATGG TGACGGTAACGTTGGCACTCTTCG TGAAGTCCGAGTCATCTCCGGGCT GCCAGCTGTT |
| SEQ ID No: 22 | 10.1 | 17.11 | TCCCCAAGCTTATAAACACTTCGT CAAGAGCTGCCACCTCATCGATGG TGATGGTAACGTTGGCACTCTTCG TGAAGTCCGAGTCATCTCCGGGCT GCCAGCTGTT |
| SEQ ID No: 23 | 10.1 | 17.12 | TGTACTAACTCATGCCCTCTTCTT ACCATCGGAGTTTGTTCTCTCCGT TCCGCAATTGCCAGAGCGGACGAA AAACCGCCTGAGAGTACGCCGCAA CCTCTGTCG |
| SEQ ID No: 24 | 10.1 | 17.12 | TGTACTAACTCATGCCCTCTTCTT ACCATCGGAGTTTGTTCTCTCCGT TCAGCAATTGCCAGAGCGGACGAA AAACCGCCTGAGAGTACGCCGCAA CCTCTGTCG |
| SEQ ID No: 25 | 10.1 | 18.02 | CGTCATCATCGTCATCTTCATCAG CATCTTCACCACCAAACCTYTGGT TCATCAAATCTTCCCTGGAATACA TTTGCATACCGGGGCTCCAGGCA TATCCTGAAGGCAAAATGTTGTAA ATTTCAAATTCTGACTCACG |
| SEQ ID No: 26 | 10.1 | 18.02 | CGTCATCATCGTCATCTTCATCAG CATCTTCACCACCAAACCTYTGGT TCATCAAATCTTCCCTGGAATACA TTTGCATACCAGGGGCTCCAGGCA TATCCTGAAGGCAAAATGTTGTAA ATTTCAAATTCTGACTCACG |

The SNP sequences of the markers SEQ ID No:1, SEQ ID No:3, SEQ ID No:5, SEQ ID No:7 and SEQ ID No:9 are in the genome of seeds of the deposit NCIMB 42140 linked to QTL1 of the invention and the SNP sequences of the markers SEQ ID No:15, SEQ ID No:17, SEQ ID No:19, SEQ ID No:21, SEQ ID No:23 and SEQ ID No:25 are in the genome of seeds of the deposit NCIMB 42138 linked to QTL2 of the invention. The SNP sequences of markers of SEQ ID No:11 and SEQ ID No:13 are in the genome of seeds of the deposit NCIMB 42138 linked to QTL3, which QTLs each confer the increased total terpenoid content to fruits of pepper plants. These SNP sequences can be used as molecular markers for increased total terpenoid content of fruits of plants grown from seeds from said deposit.

The sequences of SEQ ID No:2, SEQ ID No:4, SEQ ID No:6, SEQ ID No:8, SEQ ID No:10, SEQ ID No:12, SEQ ID No:14, SEQ ID No:16, SEQ ID No:18, SEQ ID No:20, SEQ ID No:22, SEQ ID No:24 and SEQ ID No:26 represent the wildtype C. annuum alleles for the molecular SNP markers SEQ ID No:1, SEQ ID No:3, SEQ ID No:5, SEQ ID No:7, SEQ ID No:9, SEQ ID No:11, SEQ ID No:13, SEQ ID No:15, SEQ ID No:17, SEQ ID No:19, SEQ ID No:21, SEQ ID No:23 and SEQ ID No:25, respectively.

The nucleotides that differ between the marker and the wildtype C. annuum are underlined.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Development of a Pepper Plant with an Increased Total Terpenoid Content

The Capsicum baccatum var. pendulum accession PEN45 was used as donor parent for backcrossing (BC) with three cultivated Capsicum annuum blocky breeding lines (MT, SM and GNM). Because of difficulties in interspecific crossing, a multi-parent $BC_2$ population, consisting of three sub-populations, was generated for linkage map development. The largest PEN45 $BC_2$ sub-population out of the three, with the blocky parents SM and GNM in its pedigree, was chosen to study fruit characteristics in more detail. In this population 34 of the in total 54 $BC_2$ plants gave sufficient inbred seeds to grow $BC_2S_1$ lines. In 2009 the 34 $BC_2S_1$ lines were grown in plots of 5-9 plants with, if possible, 2 repetitions (possible for 23 $BC_2S_1$ lines) in a randomized block design. Plants were grown in soil in a greenhouse in De Lier, The Netherlands, with 2 stems per plant and with 2.5 plants/m².

Due to the generation ($BC_2S_1$) of the material and the presence of two different breeding lines (SM and GNM) in their pedigree, the lines were still segregating for several traits. To grow the $BC_2S_1$ lines as uniformly as possible, plants were pre-selected with a marker based on the Pun1 locus for non-pungent plants and with a marker based on the CCS gene (capsanthin-capsorubin synthase) for non-red (i.e. yellow or orange) plants. To compensate for selection against Pun1 or CCS linked PEN45 fragments with potentially interesting characteristics, two and five $BC_2S_1$ lines (out of the 34 lines) were used to select plants with homozygous pungent orange fruits and homozygous non-pungent red fruits, respectively. These plants were also grown in 2 repetitions with plots of 5 plants. Genotypes SM, GNM and PEN45 were grown as controls in four repetitions.

At the time of maturation of the first fruits the BC2S1 plots were made phenotypically more uniform by removing the most aberrant, mainly sterile, plants from the plots. In total 25 of the $BC_2S_1$ lines were uniform for orange color, the other 9 lines were segregating for plants with either orange or yellow fruits. In the end 250 $BC_2S_1$ plants remained in 69 plots (1-6 plants) and were used for QTL mapping, of which 160 orange, 61 yellow and 29 red fruited plants.

Three different $BC_2S_1$ plants, derive from three different $BC_2$ plants, were used to develop near-isogenic lines (NILs) by one generation of backcrossing with GNM followed by two selfing steps. A NIL population consists of genetically homogeneous lines, which only differ from each other by the presence of (different) single or only a limited number of introgression fragments from a donor parent. In this case, the donor parent is the accession PEN45, the C. baccatum parent.

Each generation (i.e. both backcrossing and selfing steps) was genotyped with SNPs flanking the original $BC_2S_1$ introgressions to obtain lines with a limited number of introgressions in a GNM genetic background. In 2011 23 NILs and the recurrent parent (GNM) were grown in three repetitions with 5 plants per plot in a completely randomized setup. Plants were grown under similar conditions as the $BC_2S_1$ lines in a greenhouse, this time in autumn and on rockwool.

Example 2

Sampling of Pepper Fruits for Biochemical Analysis

Ripe fruits (95-100% colored) from the second fruit set were used for biochemical measurements. Fruits were stored after harvesting in a climate room at 20° C. with 80% relative humidity for 3-4 days to optimize ripening. This is a procedure to mimic the Dutch commercial system. Fruits were washed with cold running tap water, dried with a clean towel, cut (top and bottom parts were discarded) in 1-2 cm pieces, these pieces were mixed and seeds were removed. Half of the fruit pieces from each sample were immediately frozen in liquid nitrogen, ground in an electric mill and stored at −80° C. for later biochemical analysis.

Fruits of the BC2S1 plants were harvested per plot and in case of plots segregating for plants with either orange or yellow fruits, the two colors were bulked separately. 56 BC2S1 plots (37 orange, 15 yellow and 4 red) gave sufficient fruits to make representative fruit samples of 5-8 fruits for biochemical evaluation. In addition 32 samples were made up of plots and/or individual plants that did only gave enough fruits for biochemical evaluation or that were pungent.

In the NIL experiment, 20 NILS and GNM gave sufficient fruits and were evaluated as bulks per plot.

Example 3

Metabolic Profiling and QTL Analysis

The biochemical profiling of both the BC2S1 and the NILS experiments was performed as described in Eggink et al. (Food Chemistry (2012) 132, 301-310). In the BC2S1 experiment 92 pepper fruit samples were analyzed, among which samples of fruits of the *C. annuum* parent line GNM and samples of fruits of the commercial orange blocky *C. annuum* hybrid reference line Orange Glory.

In short, the profiling of volatile metabolites was performed using headspace SPME-GC-MS. Derived GC-MS profiles were processed by the MetAlign™ software package (http://www.metalign.nl) for baseline correction, noise estimation and ion-wise mass spectral alignment. The Multivariate Mass Spectral Reconstruction (MMSR) approach (Tikunov et al., Metabolomics (2012) 8, 714-718) was used to reduce data to volatile compound mass spectra. Each compound was represented by a single selective ion fragment in the following multivariate data analysis. The compounds (number of fragment ions in a mass spectrum≥5) were then subjected to a tentative identification using the NIST mass spectral library (http://www.nist.gov). Reliable identities were assigned to compounds with a mass spectra match factor≥600. Volatile compound abundance (intensity) is represented as the height of a selective mass peak of a compound detected in chromatograms by MetAlign software. Intensities which were below the detection limit in certain genotypes, obtained a random value between 250 and 500.

In the BC2S1 experiment in total 222 putative volatile compounds were detected, of which 22 volatiles were specific to PEN45 (i.e. under detection limit in all BC2S1 plants and *C. annuum* parents). Putative identities could be assigned to 178 of these. In the ML experiment in total 137 putative volatile compounds were detected. Identities were assigned to 96 of these.

The 250 BC2S1 plants from the PEN45 BC2 sub-population having the blocky parents SM and GNM in its pedigree, were genotyped with 239 SNPs that were polymorphic in PEN45 versus SM and GNM. Interval mapping, with separate sessions for metabolites (200 volatiles and 6 non-volatiles, 88 plots or plants) and several physical fruit characteristics (either on 250 plants or 76 plots), allowed identification of QTLs within all trait classes.

The Interval Mapping method within the program MapQTL 6 (Van Ooijen, MapQTL 6: software for the mapping of quantitative trait loci in experimental populations of diploid species (2009) Kyazma B V, Wageningen) was used for QTL identification in the BC2S1 experiment. A permutation test was applied to each data set (1000 permutations) to determine the LOD (Logarithm of odds) thresholds. A genome wide (GW) LOD threshold of 2.7 was used for QTL significance (p<0.05). The chromosomal locations with the highest LOD scores were considered to be the most likely positions of a QTL. Graphics were produced by MapChart software (Voorrips, Journal of Heredity (2002) 93, 77-78). The ML experiment was analyzed using the non-parametric Kruskal-Wallis test within MapQTL 6 to identify markers that showed significant (p<0.05) trait associations. The analyses in both experiments were performed with log 2 transformed metabolite data.

An initial analysis of the 137 metabolites detected in the NILs by principal components analysis made it clear that a large part of the metabolic variation between the genotypes is caused by a group of terpenoids. A large variation in terpenoid levels was found, with for some terpenes a maximum concentration which was almost 40 fold higher than detected in the most extreme parent. For terpenoids linalooloxide and p-menth-1-en-9-al a major QTL (LOD>10) on LG10.1 and a p-menth-1-en-9-al specific QTL (LOD 4.1) on LG1 were found (Table 1).

Taking a closer look at the NILs having these LG10.1 (NIL45, 48 and 54) or LG1 (NIL36 and 47) introgression revealed they had major effects on the terpenoid content of the mature fruits, affecting at least fifteen different terpenoids (Table 1). The QTLs on LG10.1 and LG1 affected the accumulation of monoterpenes only, whereas sesquiterpenes and diterpenes were unaffected by these two introgressions. In most cases, both introgressions resulted in up-regulation of the same compounds, some terpenoids, however, were specifically affected by one of the two introgressions. For cineole only the LG1 introgression was effective and for (E)-β-ocimene the up-regulation was specific to the LG10.1 introgression present in NIL45 (NCIMB 42138) and NIL54 (QTL3). The effect of the LG10.1 introgression was supported by a significant QTL in both the BC2S1 population and the NILs (Table 1).

The size of the LG1 and LG10.1 introgression fragment is 4.6 cM for QTL1, whereas the size of the LG10.1 introgression fragments is 2.5 cM for QTL2 and 6.3 cM for QTL3. QTL2 and QTL3 together are located on an introgression fragment of 18.0 cM. These sizes are based on the genetic map (FIG. 2) developed within the research leading to this invention. The availability of in-fragment markers facilitates their use in breeding. Nomenclature of linkage groups is referred to the consensus chromosome numbers as in Wu et al. (Theor. Appl. Genet. (2009) 118, 1279-1293).

Fruits of NIL36 (NCIMB 42140) and 47, containing the LG1 introgression affecting terpenoid content, have a similar size and fruit color as the recurrent parent, making them amenable for direct use in breeding.

TABLE 1

LG10.1 and LG1 terpenoid QTLs

| | | | | | BC2S1 population | | | | | | | | NILs | | | |
|---|---|---|---|---|---|---|---|---|---|---|---|---|---|---|---|---|
| Compound | EC[1] | LG [2] | LOD | % EV | μA | μH | μB | Add. | PEN45 | GNM | OG | Signif. | mA | mB | A/B |
| α-Terpinene | $C_{10}H_{16}$ | 10.1 | 4.3 | 20.2 | 13.9 | 14.8 | 15.7 | −0.88 | 13.4 | 14.3 | 15.0 | 0.0001 | 10.7 | 13.2 | 54/9 |
| | | 1 | 0.0 ns | 0.0 | 14.3 | 14.3 | 14.3 | 0.02 | | | | 0.001 | 10.9 | 13.2 | 57/6 |
| γ-Terpinene | $C_{10}H_{16}$ | 10.1 | 8.3 | 35.3 | 12.0 | 13.7 | 15.3 | −1.62 | 13.8 | 11.3 | 11.0 | 0.0001 | 10.4 | 12.8 | 54/9 |
| | | 1 | 2.3 ns | 11.0 | 12.4 | 13.4 | 14.3 | −0.94 | | | | 0.001 | 10.5 | 12.9 | 57/6 |
| Terpinolene | $C_{10}H_{16}$ | 10.1 | 10.3 | 41.7 | 14.7 | 16.7 | 18.7 | −2.00 | 16.2 | 13.7 | 13.9 | 0.0001 | 12.4 | 15.3 | 54/9 |
| | | 1 | 2.3 ns | 11.1 | 15.2 | 16.3 | 17.3 | −1.07 | | | | 0.001 | 12.6 | 15.2 | 57/6 |
| Limonene | $C_{10}H_{16}$ | 10.1 | 10.4 | 42.0 | 15.3 | 16.6 | 18.0 | −1.35 | 18.0 | 14.8 | 14.7 | 0.0001 | 13.6 | 16.4 | 54/9 |
| | | 1 | 0.8 ns | 3.9 | 15.8 | 16.2 | 16.6 | −0.43 | | | | 0.005 | 13.8 | 16.1 | 57/6 |
| Myrcene | $C_{10}H_{16}$ | 10.1 | 7.3 | 31.8 | 12.0 | 15.1 | 18.3 | −3.18 | 16.2 | 8.6 | 12.2 | 0.0001 | 11.7 | 14.7 | 54/9 |
| | | 1 | 1.7 ns | 8.5 | 12.7 | 14.2 | 15.6 | −1.45 | | | | 0.001 | 11.8 | 14.8 | 57/6 |
| (E)-β-Ocimene | $C_{10}H_{16}$ | 10.1[3] | 2.9 | 14.1 | 14.3 | 15.5 | 16.8 | −1.23 | 14.5 | 15.4 | 16.0 | 0.0005 | 12.5 | 15.1 | 57/6 |
| Hotrienol | $C_{10}H_{16}O$ | 10.1 | 5.9 | 26.5 | 14.2 | 17.2 | 20.2 | −2.98 | 15.6 | 13.9 | 12.8 | 0.0001 | 9.7 | 14.6 | 54/9 |
| | | 1 | 3.0 | 14.6 | 14.7 | 16.6 | 18.6 | −1.96 | | | | 0.005 | 10.0 | 14.0 | 57/6 |
| p-Menth-1-en-9-al | $C_{10}H_{16}O$ | 10.1 | 10.2 | 41.4 | 16.3 | 18.5 | 20.7 | −2.24 | 16.1 | 14.9 | 15.2 | 0.0001 | 14.9 | 18.3 | 54/9 |
| | | 1 | 4.1 | 19.1 | 16.6 | 18.0 | 19.3 | −1.35 | | | | 0.0005 | 15.0 | 18.6 | 57/6 |
| Geranic-oxide | $C_{10}H_{18}O$ | 10.1 | 10.6 | 42.6 | 15.8 | 16.9 | 18.0 | −1.10 | 15.0 | 15.5 | 15.3 | 0.0005 | 13.6 | 14.6 | 54/9 |
| | | 1 | 0.4 ns | 2.1 | 16.2 | 16.5 | 16.7 | −0.26 | | | | 0.005 | 13.7 | 14.4 | 57/6 |
| Myrcenol | $C_{10}H_{18}O$ | 10.1 | 10.5 | 42.2 | 11.5 | 13.8 | 16.1 | −2.31 | 11.4 | 11.3 | 10.7 | 0.0001 | 9.8 | 13.2 | 54/9 |
| | | 1 | 1.6 ns | 8.0 | 12.1 | 13.2 | 14.2 | −1.04 | | | | 0.005 | 10.0 | 12.8 | 57/6 |
| α-Terpineol | $C_{10}H_{18}O$ | 10.1 | 10.7 | 42.8 | 17.9 | 20.2 | 22.7 | −2.44 | 18.0 | 16.7 | 17.2 | 0.0001 | 16.4 | 19.3 | 54/9 |
| | | 1 | 2.9 | 14.2 | 18.3 | 19.5 | 20.8 | −1.24 | | | | 0.005 | 16.6 | 19.2 | 57/6 |
| Linalool | $C_{10}H_{18}O$ | 10.1 | 9.5 | 39.3 | 16.9 | 19.5 | 22.1 | −2.62 | 17.4 | 15.2 | 16.3 | 0.0001 | 16.0 | 18.1 | 54/9 |
| | | 1 | 2.6 ns | 12.7 | 17.4 | 18.7 | 20.1 | −1.31 | | | | 0.005 | 16.2 | 17.8 | 57/6 |
| Cineole | $C_{10}H_{18}O$ | 1 | 6.8 | 29.8 | 12.0 | 14.7 | 17.3 | −2.62 | 15.8 | 10.5 | 8.6 | 0.0001 | 9.2 | 14.6 | 57/6 |
| (E)-Linalooloxide | $C_{10}H_{18}O_2$ | 10.1 | 11.0 | 43.9 | 16.7 | 19.1 | 21.5 | −2.41 | 15.6 | 15.8 | 15.2 | 0.0001 | 15.2 | 18.7 | 54/9 |
| | | 1 | 2.7 | 13.0 | 17.2 | 18.4 | 19.5 | −1.16 | | | | 0.001 | 15.3 | 18.8 | 57/6 |
| Linalooloxide | $C_{10}H_{18}O_2$ | 10.1 | 11.1 | 44.1 | 15.0 | 17.3 | 19.6 | −2.29 | 14.0 | 14.1 | 13.6 | 0.0001 | 13.8 | 17.1 | 54/9 |
| | | 1 | 2.5 ns | 12.2 | 15.6 | 16.6 | 17.7 | −1.07 | | | | 0.001 | 13.9 | 17.3 | 57/6 |

Legend table 1
[1] Elemental composition
[2] LG10.1 and LG1 refer to markers SEQ ID No:17 at 16.6 cM and SEQ ID No:1 at 20.2 cM, respectively, on the corresponding linkage groups
[3] Refers to marker SEQ ID No:13 at 6.3 cM on LG10.1
Percentage of explained variance (% EV), estimated (n, Van Ooijen, MapQTL 6: software for the mapping of quantitative trait loci in experimental populations of diploid species (2009) Kyazma BV, Wageningen) or direct means (m), estimated additive effect (add.) and genotype distribution (AB) are given. Metabolite values represent log2 values of peak intensities.
ns = not significant

Example 4

Anthracnose Field Trial

To test whether the fruits of plants of the invention were more resistant to anthracnose infection an anthracnose field test in a tropical climate was set up in three replicates with plots of 15-20 plants each in a randomized (block) design. Susceptible control lines that were included were NuMex RNaky, Early Jalapeno and CM334. Seven NILs, including three randomly selected NILs not carrying any QTL of the invention, four NILs with increased terpene concentrations (NIL36 and NIL47 with introgression LG1 (QTL1), NIL45 with introgression LG10.1 (QTL2 plus QTL3), and NIL48 with introgression LG10.1 (QTL2)), and the recurrent parent (GNM) were included.

From the moment on that the first green fruits were fully grown, on a weekly basis the following characteristics were recorded: number of plants per plot, number of infected green fruits per plot (these fruits were removed in order not to be counted again when they were red), number of harvested red fruits per plot, number of infected red fruits that are harvested per plot. Any infection level was counted as an infected fruit, irrespective of the amount and sizes of the lesions. Infection level was expressed as percentage of infected green or red fruits.

The infection level of fruits from plants of the invention, was lower than that of fruits of GNM plants or fruits from plants with random NILs not carrying any of the QTLs of the invention.

Example 5

Indirect Defense Test

To test whether plants of the invention were better at attracting natural enemies of herbivores that feed on pepper by, for example, the production of herbivore-induced volatiles that attract the natural enemies of the herbivore, a test was done to determine the attractiveness of plants of the invention to natural enemies after induction of their indirect defense response by either herbivore infestation or JA-treatment, mimicking herbivore infestation. Eight NILs, including three randomly selected NILs not carrying any QTL of the invention, five NILs with increased terpenoid concentrations (NIL36 and NIL47 with introgression LG1 (QTL1), and NIL48 (QTL2) and NIL45 and NIL54 (QTL2 plus QTL3) with introgression LG10.1), and the recurrent parent (GNM) were grown. Seeds were sown in potting compost in small containers (Ø 5 cm) and grown in a climate chamber for 8 weeks (8 hrs light, 21° C.). Non-infested plants were then re-potted into larger containers (Ø 16 cm) and transferred to a greenhouse where they could grow to mature plants with normally sized leaves. These plants were used for attractiveness experiments using induction by spider mite infestation or JA treatment.

For JA-induction plants were treated with JA by spraying plants with 1 ml of 1 mM JA+0.001% of Tween-80 solution per plant. For spider mite infestation, mites were grown on lima bean plants and transferred individually to the Capsicum plants using a fine brush. For infestation experiments, 50 spider mites were equally distributed over a single plant. Plants were analysed 10 days after the start of infestation.

The relative attractiveness to *Phytoseiulus persimilis* and *Amblyseius swirski* predatory mites to the odor blend of the different JA-induced accessions and the spider mite infested accessions was tested in two multiple choice set-ups. In the first set-up an arena was made of 10 oasis blocks placed in a circle with a diameter of 40 cm. The inner part of the arena was filled with sandy soil. Pepper plants were induced by application of JA as described above and detached leaves of each sweet pepper accession were randomly placed in wet oasis blocks. Similar leaf areas were used for each accession as judged by the eye. Leaf areas were determined at the end of the experiment. The arena experiment was performed in triplicate for each predatory mite species, and in each experiment accessions were placed differently. Predatory mites were released in the centre of the arena and after 4-8 hrs, depending on the experiment, the number of predatory mites on each of the leaves was counted using a stereo microscope. In the second set-up JA-treated plants were tested in a two-choice Y-olfactometer. Odor sources consisted of detached leaves previously induced with JA, 24 hrs prior to the experiment. Individual predators were released on an iron wire in the basal tube, and their behavior was observed for a maximum of 5 min. The connections of the odor sources to the arms of the olfactometer were interchanged after each series of 5 predators. A choice was recorded when the finish line, halfway one of the olfactometer arms, was reached within this period. Otherwise it was recorded as no-choice. Each predator was only used once. Per experimental day 20 predators were tested for each odor combination and each experiment was repeated on 3 different days.

Both multiple choice experiments showed that plants of the invention were more attractive to a predatory mites that GNM plants or plants with random NILS not carrying any of the QTLs of the invention.

Example 6

Spider Mite Development Test

To test whether plants of the invention had an increased level of resistance to spider mites (*Tetranychus urticae*), a test was done to compare spider mite development on plants of the invention and control plants. Eight NILS, including three randomly selected NILS not carrying any QTL of the invention, five NILS with increased terpenoid concentrations (NIL36 and NIL47 with introgression LG1 (QTL1), and NIL48 (QTL2) and NIL45 and NIL54 (QTL2 plus QTL3) with introgression LG10.1), *Capsicum baccatum* var. *pendulum* PEN45 and the recurrent parent (GNM) were grown in the greenhouse for 5 to 6 weeks. Only plants that looked healthy, i.e. showed no infestation by either pests or pathogen as judged by the eye, were used for the experiments (non-induced plants).

Leaf discs (Ø 1.5 cm) from young but fully developed leaves were placed upside down on well-plates filled with water agar (2%). Spider mites were reared on lima bean plants for more than 100 generations. Mites were transferred to new bean plants and allowed to oviposit for 1 day and subsequently discarded. Bean plants with spider mite eggs were maintained under greenhouse conditions for 9 days. The mites developed from these eggs were considered to be of the same age, to have had a mating experience and were used for the experiments.

Single mites were placed on the *Capsicum* leaf discs with a very fine brush (single hair) and kept for 5 days at 20° C. After 1 day it was checked if the mite was still alive or otherwise the leaf-mite combination was discarded from the assay. After 5 days, the number of eggs laid by the mites was counted. All accessions were tested in 3 individual experiments, that were performed in the period October-March in a greenhouse in The Netherlands with supplemental lighting. An experiment consisted of 9 leaf discs for each accession.

All five NILS with increased terpenoid concentrations (NIL36 and NIL47 with introgression LG1 (QTL1), and NIL48 (QTL2) and NIL45 and NIL54 (QTL2 plus QTL3) with introgression LG10.1) showed a significantly lower spider mite egg deposition compared to recurrent parent GMN, the three randomly selected NILS (A, B and C) not carrying any QTL of the invention and *Capsicum baccatum* var. *pendulum* PEN45 (FIG. 3). The decrease in spider mite egg deposition compared to plants not carrying any QTL of the invention was most clear in plants of the invention carrying both QTL2 and QTL3 (NIL45 and NIL54). The development of spider mites was thus seriously hampered by the presence of the trait of the invention. This showed that plants of the invention had a higher level of resistance to spider mites that GNM plants, *Capsicum baccatum* var. *pendulum* PEN45, or plants with random NILS not carrying any of the QTLs of the invention.

The invention is further described by the following numbered paragraphs:

1. A pepper plant (*Capsicum annuum* L.) that produces fruits with an increased total content of terpenoids as a result of the presence in the genome of the pepper plant of at least one QTL selected from QTL1, QTL2 and QTL3, wherein:
   QTL1 is the same or similar to the QTL that in the genome of plants grown from seeds of deposit NCIMB 42140 is located on LG1 and is linked therein to at least one marker selected from the group consisting of SEQ. No:1, SEQ ID No:3, SEQ ID No:5, SEQ ID No:7 and SEQ ID No:9;
   QTL2 is the same or similar to the QTL that in the genome of plants grown from seeds of deposit NCIMB 42138 is located on LG10.1 and is linked therein to at least one marker selected from the group of SEQ ID No:15, SEQ ID No:17, SEQ ID No:19, SEQ ID No:21, SEQ ID No:23 and SEQ ID No:25; and
   QTL3 is the same or similar to the QTL that in the genome of plants grown from seeds of deposit NCIMB 42138 is located on LG10.1 and is linked therein to at least one marker selected from the group of SEQ ID No:11 and SEQ ID No:13.

2. A pepper plant of paragraph 1, wherein:
   QTL1 is the same or similar to the QTL that in the genome of plants grown from seeds of deposit NCIMB 42140 is located on LG1 and is linked therein to markers SEQ. No:1, SEQ ID No:3, SEQ ID No:5, SEQ ID No:7 and SEQ ID No:9;
   QTL2 is the same or similar to the QTL that in the genome of plants grown from seeds of deposit NCIMB 42138 is located on LG10.1 and is linked therein to markers ID No:15, SEQ ID No:17, SEQ ID No:19, SEQ ID No:21, SEQ ID No:23 and SEQ ID No:25; and
   QTL3 is the same or similar to the QTL that in the genome of plants grown from seeds of deposit NCIMB 42138 is located on LG10.1 and is linked therein to markers SEQ ID No:11 and SEQ ID No:13.

3. A pepper plant of paragraph 1 or 2, wherein QTL1 is as present in the genome of, or obtainable from, *Capsicum baccatum* plants or pepper plants grown from seed a representative sample of which was deposited at the NCIMB under number NCIMB 42140, and wherein QTL2 and QTL3 are as present in the genome of, or obtainable from, *Capsicum baccatum* plants or pepper plants grown from seed of which a representative sample was deposited at the NCIMB under number NCIMB 42138.

4. A pepper plant of any of the paragraphs 1-3, wherein the fruits of a pepper plant carrying QTL1 and/or 2 have an increased total content of terpenoids, in particular an increased concentration of one or more monoterpenoids, in particular monoterpenoids selected from the group consisting of α-Terpinene, γ-Terpinene, Terpinolene, Limonene, Myrcene, Hotrienol, p-Menth-1-en-9-al, Geranic-oxide, Myrcenol, α-Terpineol, Linalool, Cineole, (E)-Linalooloxide and Linalooloxide, as compared to pepper fruits of a similar ripening stage from isogenic plants not carrying QTL1 and/or QTL2, and wherein the fruits of a pepper plant carrying QTL3 have an increased concentration of (E)-β-Ocimene, as compared to pepper fruits of a similar ripening stage from isogenic plants not carrying QTL3.

5. A pepper plant of any one of the paragraphs 1-4, comprising QTL1 or QTL2 or QTL3 or QTL1 plus QTL2 or QTL1 plus QTL3 or QTL2 plus QTL3 or QTL1 plus QTL2 plus QTL3.

6. A pepper plant of any one of the paragraphs 1-5, wherein at least one of the QTLs is homozygously present.

7. Seed of a pepper plant of any one of the paragraphs 1-6, or seed capable of growing into such a pepper plant, comprising at least one of QTL1, QTL2 and QTL3 and wherein at least one of the QTLs is preferably homozygously present.

8. Progeny of a pepper plant of any one of the paragraphs 1-6 or progeny of pepper plants grown from seeds of paragraph 7, wherein the progeny of the plant comprises at least one of QTL1, QTL2 and QTL3, and wherein at least one of the QTLs is preferably homozygously present.

9. Propagation material derived from a pepper plant of any one of the paragraphs 1-6 or 8 or from pepper seeds of paragraph 7, wherein the propagation material comprises at least one of QTL1, QTL2 and QTL3, and wherein at least one of the QTLs is preferably homozygously present.

10. Propagation material capable of growing into a pepper plant of any one of the paragraphs 1-6.

11. Propagation material of paragraph 9 or 10, wherein the propagation material is selected from the group consisting of callus, microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds and stems or parts or tissue culture thereof.

12. A pepper fruit, or parts thereof, obtainable from a pepper plant of any one of the paragraphs 1-6 or 8, or a plant grown from seeds of paragraph 7, comprising at least one of QTL1, QTL2 and QTL3.

13. A food product or a processed food product comprising a pepper fruit or a part thereof of paragraph 12.

14. The use of a pepper plant of any one of the paragraphs 1-6 or 8 as germplasm in a breeding program for the development of pepper plants producing fruits with an increased total content of terpenoids, in particular an increased concentration of at least one compound selected from the group consisting of α-Terpinene, γ-Terpinene, Terpinolene, Limonene, Myrcene, (E)-β- Ocimene, Hotrienol, p-Menth-1-en-9-al, Geranic-oxide, Myrcenol, α-Terpineol, Linalool, Cineole, (E)-Linalooloxide and Linalooloxide.

15. A nucleic acid or a part thereof, optionally in isolated form, which causes an increased total content of terpenoids in pepper fruits, which nucleic acid originates from LG1 of a *Capsicum baccatum* plant or a pepper plant of any one of the paragraphs 1-6, and is linked thereon to at least one of the molecular markers selected from the group of SEQ ID NO:1, SEQ ID No:3, SEQ ID No:5, SEQ ID No:7 and SEQ ID NO:9 or originates from LG10.1 of a *Capsicum baccatum* plant or a pepper plant of any one of the paragraphs 1-4, and is linked thereon to at least one of the molecular markers selected from the group of SEQ ID NO:11, SEQ ID No:13 and/or SEQ ID No:15, SEQ ID No:17, SEQ ID No:19, SEQ ID NO:21, SEQ ID No:23 and SEQ ID No:25.

16. Use of a molecular marker selected from the group consisting of SEQ ID No:1, SEQ ID No:3, SEQ ID No:5, SEQ ID No:7, SEQ ID No:9, SEQ ID No:11, SEQ ID No:13, SEQ ID No:15, SEQ ID No:17, SEQ ID No:19, SEQ ID No:21, SEQ ID No:23 and SEQ ID No:25 to identify or develop pepper plants producing fruits that have an increased total content of terpenoids, in particular as in paragraph 4, and/or to identify QTL1 and/or QTL2 and/or QTL3, and/or to develop other markers linked to QTL1, QTL2 and/or QTL3.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A *Capsicum annuum* plant that produces a fruit with an increased total content of terpenoids as a result of the presence in the genome of the *Capsicum annuum* plant of a QTL2 from *Capsicum baccatum* var. pendulum, as compared to the total content of terpenoids of a pepper fruit of a similar ripening stage from an isogenic *Capsicum annuum* plant not carrying QTL2, wherein the plant is a sweet pepper plant and wherein:

QTL2 is present in the genome of plants grown from seeds of NCIMB deposit accession number 42138, wherein said *Capsicum annuum* plant comprising said QTL from *Capsicum baccatum* also comprises SEQ ID No:15, SEQ ID No:17, SEQ ID No:19, SEQ ID No:21, SEQ ID No:23 and SEQ ID No:25.

2. The plant of claim 1, wherein the terpenoids comprise a monoterpenoid.

3. The plant of claim 2, wherein the monoterpenoid is α-terpinene, γ-terpinene, terpinolene, limonene, myrcene, hotrienol, p-menth-1-en-9-al, geranic-oxide, myrcenol, α-terpineol, linalool, cineole, (e)-linalooloxide or linalooloxide.

4. The plant of claim 1 comprising QTL1 plus QTL2 or QTL2 plus QTL 3 or QTL1 plus QTL2 plus QTL3 wherein:

QTL1 is present in the genome of plants grown from seeds of deposit NCIMB 42140 on LG1 and is linked to at least one marker selected from the group consisting of SEQ. No:1, SEQ ID No:3, SEQ ID No:5, SEQ ID No:7 and SEQ ID No:9; and QTL3 is present in the genome of plants grown from seeds of deposit NCIMB 42138 on LG10.1 and is linked to at least one marker selected from the group of SEQ ID No:11 and SEQ ID No:13.

5. The plant of claim 1, wherein QTL2 is homozygously present.

6. A seed of the plant of claim 1, or a seed capable of growing into the plant of claim 1, wherein the seed comprises QTL2 as defined in claim 1.

7. The seed of claim 6, wherein QTL2 is homozygously present.

8. The *Capsicum annuum* progeny of the plant of claim 1, wherein the progeny of the plant comprises QTL2 as defined in claim 1.

9. The progeny of claim 8, wherein QTL2 is homozygously present.

10. The *Capsicum annuum* progeny of the plant grown from the seed of claim 6, wherein the progeny of the plant comprises QTL2.

11. The progeny of claim 10, wherein QTL2 is homozygously present.

12. A *Capsicum annuum* propagation material derived from the plant of claim 1, wherein the propagation material comprises QTL2 as defined in claim 1.

13. The propagation material of claim 12, wherein QTL2 is homozygously present.

14. A *Capsicum annuum* propagation material derived from a plant grown from the seed of claim 6, wherein the propagation material comprises QTL2.

15. The propagation material of claim 14, wherein QTL2 is homozygously present.

16. A *Capsicum annuum* propagation material capable of growing into the plant of claim 1, wherein the propagation material comprises QTL2 as defined in claim 1.

17. The propagation material of claim 12, wherein the propagation material comprises a callus, microspore, pollen, ovary, ovule, embryo, embryo sac, egg cell, cutting, root, stem, cell, protoplast, leaf, cotyledons hypocotyl, meristematic cell, root, root tip, microspore, anther, flower, seed or stem or a part or tissue culture thereof.

18. The propagation material of claim 14, wherein the propagation material comprises a callus, microspore, pollen, ovary, ovule, embryo, embryo sac, egg cell, cutting, root, stem, cell, protoplast, leaf, cotyledons hypocotyl, meristematic cell, root, root tip, microspore, anther, flower, seed or stem or a part or tissue culture thereof.

19. The propagation material of claim 16, wherein the propagation material comprises a callus, microspore, pollen, ovary, ovule, embryo, embryo sac, egg cell, cutting, root, stem, cell, protoplast, leaf, cotyledons hypocotyl, meristematic cell, root, root tip, microspore, anther, flower, seed or stem or a part or tissue culture thereof.

20. A pepper fruit, or a part thereof, obtainable from the plant of claim 1, wherein the pepper fruit or the part thereof comprises QTL2 and as defined in claim 1.

21. A pepper fruit, or a part thereof, obtainable from a plant grown from the seed of claim 6, wherein the pepper fruit or the part thereof comprises QTL2.

* * * * *

UNITED STATES PATENT AND TRADEMARK OFFICE
CERTIFICATE OF CORRECTION

PATENT NO. : 10,206,367 B2
APPLICATION NO. : 14/979969
DATED : February 19, 2019
INVENTOR(S) : Pieter Martijn Eggink et al.

Page 1 of 1

It is certified that error appears in the above-identified patent and that said Letters Patent is hereby corrected as shown below:

In the Claims

Please correct Claim 18 at Column 44, Line 66 to Column 45, Line 4, as follows:
18. The propagation material of claim 14, wherein the propagation material comprises a callus, microspore, pollen, ovary, ovule, embryo, embryo sac, egg cell, cutting, root, stem, cell, protoplast, leaf, cotyledons hypocotyl, meristematic cell, root, root tip, microspore, anther, flower, seed or stem; or a part or tissue culture thereof.

Please correct Claim 19 at Column 45, Lines 5-10, as follows:
19. The propagation material of claim 16, wherein the propagation material comprises a callus, microspore, pollen, ovary, ovule, embryo, embryo sac, egg cell, cutting, root, stem, cell, protoplast, leaf, cotyledons hypocotyl, meristematic cell, root, root tip, microspore, anther, flower, seed or stem; or a part or tissue culture thereof.

Please correct Claim 20 at Column 45, Lines 11-13, as follows:
20. A pepper fruit, or a part thereof, from the plant of claim 1, wherein the pepper fruit or the part thereof comprises QTL2 as defined in claim 1.

Please correct Claim 21 at Column 45, Lines 14-16, as follows:
21. A pepper fruit, or a part thereof, from a plant grown from the seed of claim 6, wherein the pepper fruit or the part thereof comprises QTL2.

Signed and Sealed this
Third Day of September, 2019

Andrei Iancu
*Director of the United States Patent and Trademark Office*